(12) United States Patent
Yu

(10) Patent No.: US 11,110,303 B2
(45) Date of Patent: Sep. 7, 2021

(54) HAPTEN-ENHANCED CHEMOIMMUNOTHERAPY BY ULTRA-MINIMUM INCISION PERSONALIZED INTRATUMORAL CHEMOIMMUNOTHERAPY

(71) Applicant: Baofa Yu, La Jolla, CA (US)

(72) Inventor: Baofa Yu, La Jolla, CA (US)

( * ) Notice: Subject to any disclaimer, the term of this patent is extended or adjusted under 35 U.S.C. 154(b) by 617 days.

(21) Appl. No.: 15/529,961

(22) PCT Filed: Nov. 24, 2015

(86) PCT No.: PCT/US2015/062538
§ 371 (c)(1),
(2) Date: May 25, 2017

(87) PCT Pub. No.: WO2016/086070
PCT Pub. Date: Jun. 2, 2016

(65) Prior Publication Data
US 2019/0125778 A1    May 2, 2019

Related U.S. Application Data

(60) Provisional application No. 62/085,235, filed on Nov. 26, 2014.

(51) Int. Cl.
*A61P 35/00* (2006.01)
*A61K 31/06* (2006.01)
(Continued)

(52) U.S. Cl.
CPC .............. *A61P 35/00* (2018.01); *A61K 31/06* (2013.01); *A61K 31/166* (2013.01); *A61K 31/32* (2013.01);
(Continued)

(58) Field of Classification Search
CPC .... A61K 31/06; A61K 31/166; A61K 31/397; A61K 31/502; A61P 35/00
See application file for complete search history.

(56) References Cited

U.S. PATENT DOCUMENTS 4,160,817 A    7/1979  Bucovaz et al.
4,447,526 A    5/1984  Rupchock et al.
(Continued)

FOREIGN PATENT DOCUMENTS

CN        1431909      7/2003
EP         240191      3/1987
(Continued)

OTHER PUBLICATIONS

Goldberg EP, Hadba AR, Almond BA, Marotta JS. Intratumoral cancer chemotherapy and immunotherapy: opportunities for nonsystemic preoperative drug delivery. J Pharm Pharmacol. Feb. 2002;54(2):159-80. PMID: 11848280. (Year: 2002).*

(Continued)

*Primary Examiner* — Theodore R. Howell
(74) *Attorney, Agent, or Firm* — Knobbe Martens Olson & Bear, LLP

(57) ABSTRACT

Embodiments disclosed herein provide methods for treating neoplasm in a mammal, comprising intratumorally administering to the neoplasm an effective amount of a pharmaceutical composition comprising: a hapten; and a redox agent, whereby the neoplasm is treated.

17 Claims, 28 Drawing Sheets

(51) Int. Cl.
  A61K 31/166    (2006.01)
  A61K 31/397    (2006.01)
  A61K 31/502    (2006.01)
  A61K 45/06     (2006.01)
  A61K 31/32     (2006.01)
  A61K 31/327    (2006.01)
  A61K 33/24     (2019.01)
  A61K 31/7068   (2006.01)

(52) U.S. Cl.
  CPC .......... *A61K 31/327* (2013.01); *A61K 31/397* (2013.01); *A61K 31/502* (2013.01); *A61K 31/7068* (2013.01); *A61K 33/24* (2013.01); *A61K 45/06* (2013.01); *Y02A 50/30* (2018.01)

(56) References Cited

U.S. PATENT DOCUMENTS

| | | |
|---|---|---|
| 4,724,230 A | 2/1988 | Cone, Jr. |
| 4,832,849 A | 5/1989 | Cardin |
| 4,971,991 A | 11/1990 | Umemura et al. |
| 5,005,588 A | 4/1991 | Rubin |
| 5,156,841 A | 10/1992 | Rapp |
| 5,215,899 A | 6/1993 | Dattagupta |
| 5,290,551 A | 3/1994 | Berd |
| 5,340,803 A | 8/1994 | Rubin |
| 5,593,900 A | 1/1997 | Tryggvason et al. |
| 5,629,327 A | 5/1997 | D'amato |
| 5,651,986 A | 7/1997 | Brem et al. |
| 5,705,151 A | 1/1998 | Dow et al. |
| 5,712,291 A | 1/1998 | D'amato |
| 5,846,565 A | 12/1998 | Brem et al. |
| 6,248,585 B1 | 6/2001 | Berd |
| 6,811,788 B2 | 11/2004 | Yu |
| 7,041,302 B2 | 5/2006 | Roussel |
| 7,927,612 B2 | 4/2011 | Yu |
| 8,501,243 B2 | 8/2013 | Yu |
| 9,000,036 B2 | 4/2015 | Yu |
| 2002/0044919 A1 | 4/2002 | Yu |
| 2005/0079133 A1 | 4/2005 | Yang et al. |
| 2005/0118187 A1 | 6/2005 | Yu |
| 2010/0104660 A1* | 4/2010 | Yu .......................... A61K 31/04  424/649 |

FOREIGN PATENT DOCUMENTS

| | | |
|---|---|---|
| EP | 378888 | 1/1989 |
| FR | 2505182 | 11/1982 |
| JP | 11-171788 | 6/1999 |
| WO | WO 96/39226 | 12/1996 |
| WO | WO 97/11666 | 4/1997 |
| WO | WO 98/03195 | 1/1998 |
| WO | WO 98/40105 | 9/1998 |
| WO | WO 99/46385 | 9/1999 |
| WO | WO 00/06143 | 2/2000 |
| WO | WO 01/52868 | 7/2001 |
| WO | WO 03/104267 | 12/2003 |

OTHER PUBLICATIONS

Auerbach, et al., "Angiogensis Inhibition: A Review" *Pharmac. Ther.* (1994) 63: 265-311.

Awwad, et al., "Modification of monoclonal antibody carbohydrates by oxidation, conjugation, or deoxymannojirimycin does not interfere with antibody effector functions" *Cancer Immunol Immunother* (1994) 38: 23-30.

Barbie, et al., "Nuclear tumor suppressors in space and time" *TRENDS in Cell Biology* (2005) 15(7): 378-385.

Clark, Mike, Protein Engineering of Antibody Molecules for Prophylactic and Therapeutic Applications in Man, 1993, 4-5.

Coxon, et al., "Development of a Specific Polarisation Fluoroimmunoassay for Paraetamol in Serum" *Ann Clin Biochem* (1988) 25: 49-52 (Abstract Only).

Cripps, et al., "Phase II Randomized Study of ISIS 3521 and ISIS 5132 in Patients with Locally Advanced or Metastatic Colorectal Cancer: A National Cancer Institute of Canada Clinical Trails Group Study" *Clinical Cancer Research* (2002) 8: 2188-2192.

Dasgupta, Gargi and Jamil Momand, "Geldanamycin Prevents Nuclear Translocation of Mutant p53" *Experimental Cell Research* (1997) 237: 29-37.

Dieli, et al., "TCR $V_\alpha$ chain expression influences reactivity to the hapten TNP" *International Immunology* (1996) 9(1): 1-8.

Dima, et al., "Response of Murine Mammary Adenocarcinoma to Photodynamic Therapy and Immunotherapy" *Laser Ther.* (1990) 2: 153-160.

Edstrom, et al., "Mucosal Melanoma: Immunological Findings in a Rare Case Treated With BCG Vaccine, Autologous Tumor Cells, and Cytarabine" *Arch Otolaryngol* (1979) 105(1): 48-50.

Ferguson, et al., "Cell death and immune privilege" *Int. Re. Immunol.* (2002) 21(2-3): 153-172 (Abstract Only).

Gong, et al., "Differential Regulation of Sentrinized Proteins by a Novel Sentrin-specific Protease" *J. of Biological Chem.* (2000) 275(5): 3355-3359.

Hawkins, et al., "Clinical trails of antiangiogenic agents" *Current Opinion in Oncology* (1995) 7: 90-93.

Hino, et al., "Disappearance of pulmonary metastases by OK-432 treatment in a Case of Hepatocellular Carcinoma" *Acta Med Okayama* (1993) 47(4): 289-292.

International Search Report dated Dec. 6, 2007, issued in International Application No. PCT/CN2007/002671.

Jenks, Susan, "Blocking Angiogenesis May Help Keep Tumors Dormant" *J. Natl. Cancer Institute* (1996) 88(12): 787.

Jones, et al., "Antibodies for targeted gene therapy: extracellular gene targeting and intracellular expression" *Advanced Drug Delivery Reviews* (1998) 31: 153-170.

Karzulli, et al., "N-ethylmaleimide as oxidizing agent in biological and non-biological systems" *Boll. Soc. It. Biol. Sper.* (1985) 1(LXI): 121-127.

Krosl, et al., "Potentiation of Photodynamic Therapy-elicited Antitumor Response by Localized Treatment with Granulocyte-Macrophase Colony-stimulating Factor" *Cancer Research* (1996) 56: 3281-3286.

Lin, et al., "Non-surgical treatment of hepatocellular carcinoma" *J. Gastroenterology and Hepatology* (1997) 12(Suppl.): 5319-5328.

Mansouri, Ali, "Oxidation of human hemoglobin by sodium nitrite-effect of β-93 thiol groups" *Biochem and Biophys Research Communications* (1979) 89(2): 441-447 (Abstract Only).

Marshall, et al., "A Phase II Trial of ISIS 3521 in Patients with Metastatic Colorectal Cancer" *Clin. Colo. Cancer* (2004) 4(4): 288-274.

Martin, et al., "Negative and Positive Assays of Superoxide Dismutase Based on Hematoxylin Autoxidation" *Archives of Biochem. and Biophy.* (1987) 255(2): 329-336.

Molloy, et al., Apoptosis, but not necrosis, of infected monocytes is coupled with killing of intracellular Bacillus Calmette-Guerin, *J ExpMed*, 1994, vol. 180, No. 4, 1499-509.

Okano et al., "Antitumor agents. 43. Conversion of bruceoside-A into bruceantin" *J. Org. Chem.* (1981) 46:1138-1141.

O'Reilly, Michael S., "The preclinical evaluation of angiogensis inhibitors" *Investigational New Drugs* (1997) 15: 5-13.

Orkin, et al, "Report and Recommendations of the Panel to Assess the NIH Investment in Research on Gene Therapy" NIH (1995).

Oza, et al., "Phase II study of CGP 69846A (ISIS 5132) in recurrent epithelial ovarian cancer: an NCIC clinical trials group study (NCIC IND.116)" *Gyn. Oncology* (2003) 89: 129-133.

Rudnic, E., "Oral Solid Dosage Forms" in: Remington's Pharmaceutical Sciences, $18^{th}$ Ed., 1990, pp. 1633-1665.

Santini, et al., "The Oxidizing Agent Menadione Induces as Increase in the Intracellular Molecular Oxygen Concentration in K562 and A431 Cells: Direct Measurement Using the New Paramagnetic EPR Probe Fusinite" *Free Radical Biology & Medicine* (1996) 20(7): 915-924.

Schneider, et al., "Development of a new class of replicating viral vectors for cytolytic gene therapy" *Gene Ther.* (1999) 6(Suppl.): S5 (Abstract Only).

(56) References Cited

OTHER PUBLICATIONS

Skobelkin, et al., "Preoperative Activation of the Immune System by Low Reactive Level Laser Therapy (LLLT) in Oncologic Patients: A Preliminary Report" *Laser Therapy* (1991) 3(4): 169-176.

Todryk, et al., "Heat Shock Protein 70 Induced During Tumor Cell Killing Induces Th1 Cytokines and Targets Immature Dendritic Cell Precursors to Enhance Antigen Uptake" *J. Immunology* (1999) 163: 1398-1408.

Tolcher, et al., "A Randomized Phase II and Pharmacokinetic Study of the Antisense Oligonucleotides ISIS 3521 and ISIS 5132 in Patients with Hormone-refractory Prostate Cancer" *Clin. Cancer Research* (2002) 2530(2): 2530-2535.

Uehara, Y., "Protein kinase inhibitors—Screening of a new molecular target therapeutics" *Cancer & Chemotherapy* (1997) 24(2): 136-144 (Abstract Only).

Verma, et al., "Gene therapy—promises, problems and prospects" *Nature* (1997) 389: 239-242.

Yumita, et al., "The Increase of Generation of Superoxide Radicals and the Inhibitory Effect on Yoshida Sarcoma of Anthracycline Antitumor Agents by Ultrasound" *J. Japan Society for Cancer Therapy* (1989) 24(1): 63-68. (English Summary Only).

Zhang, et al., "Effect of radiation and tirapazamine (SR-4233) on three melanoma cell lines" *Mel. Research* (1998) 8: 510-515.

*Advanced Inorganic Chemistry: A Comprehensive Text*, F. Albert Cotton and Geoffrey Wilkinson $3^{rd}$ Ed., 1972, p. 408.

*Cancer Research*, Pan et al., 1989, vol. 49, 5048-5053 (Abstract Only).

*Drug Facts and Comparisons*, T. Burnham Ed., 2000, p. 1807.

*Fundamental Immunology*, William E. Paul, MD $3^{rd}$ Ed., 1993, 1157-1170.

*Glossary of Genetics: Classical and Molecular*, Rieger, et al. $5^{th}$ Ed., 1991, p. 422.

*Goodman & Gilman's The Pharmacological Basis of Therapeutics*, $9^{th}$ Ed., Stephen L. Eck and James M. Wilson (1996), Chapter 5, pp. 77-101.

*Journal of Immunological Methods*, Lisowski, et al., 1972, vol. 1, 341-352.

*Lasers in surgery and Medicine*, Brien et al., 1992, vol. 12, 313-317.

MeSH Term Invormaiton, *NLM Gateway*, from http://gateway.nlm.nih.gov/gw/Cmd?linkVars=SessionID%3D080526180415458006153610 . . . , obtained on May 26, 2008.

*Remington: The Science and Practice of Pharmacy*, vol. 1, Chapter 38: Stability of Pharmaceutical Products, Elizabeth B. Vadas, Ph.D., $19^{th}$ ed., 1995.

*SIGMA: Biochemicals and Reagents for Life Science Research*, (1999) p. 2399.

\* cited by examiner

A                                    B

HAPTEN-ENHANCED CHEMOIMMUNOTHERAPY BY ULTRA-MINIMUM INCISION PERSONALIZED INTRATUMORAL CHEMOIMMUNOTHERAPY

CROSS-REFERENCE TO RELATED APPLICATIONS

This application is the U.S. National Phase of International Application No. PCT/US2015/062,538, entitled HAPTEN-ENHANCED CHEMOIMMUNOTHERAPY BY ULTRA-MINIMUM INCISION PERSONALIZED INTRATUMORAL CHEMOIMMUNOTHERAPY, filed Nov. 24, 2015 and published on Jun. 2, 2016 as WO 2016/086,070, which claims priority to U.S. Provisional Application No. 62/085,235, filed Nov. 26, 2014, entitled "HAPTEN-ENHANCED CHEMOIMMUNOTHERAPY BY ULTRA-MINIMUM INCISION PERSONALIZED INTRATUMORAL CHEMOIMMUNOTHERAPY," the content of which is hereby incorporated by reference in its entirety.

BACKGROUND

Field of the Invention

The present invention relates to methods for treating neoplasms in mammals, particularly humans. More particularly, provided are methods for treating neoplasms by intratumoral administration of combinations of agents for hapten-enhanced chemoimmunotherapy.

Description of the Related Art

Pancreatic cancer, with only a 6% five-year survival rate, and a median survival of 6-9 months, remains one of the most malignant and aggressive cancers. It is the 10th most commonly diagnosed cancer, the 4th leading cause of cancer death in the United States. In 2013 approximately 45,220 people were diagnosed with this malignancy, with 38,460 attributed deaths worldwide during the period (Cancer Facts & Figures 2013. American Cancer Society). The lack of progress in prevention, early detection, and diagnosis of this disease places most patients in an advanced stage at the time of diagnosis, with only about 15-20% of all pancreatic cancer patients having borderline resectable tumors. Because most patients are non-operable, the only remaining treatment options are generally conventional chemotherapy, radiation and targeted therapy separately or combined. Gemcitabine is the current standard chemotherapy regimen for advanced pancreatic cancer. It has shown efficacy in phase II trials (Casper et al., *Invest New Drugs* (1994) 12:29-34), however phase III trials exploring gemcitabine-based combinations have failed to improve overall survival (OS) (Moore et al., *J Clin Oncol* (2007) 25:1960-66). Thus the need for optimal treatments in advanced pancreatic cancer remains high.

Lung cancer remains the leading cause of cancer-related deaths, accounting for about 14% (228,190 cases) in total cases and 27% (159,480 deaths) of all cancer deaths in 2013 in the United States (Jemal et al., *CA: Cancer J Clin.* (2011) 61:60-90; Cancer Facts & Figures 2013. American Cancer Society). Routine clinical treatments include surgery, radiation therapy and chemotherapy. The 5-year survival rate for all stages combined, however, is only 16% (Jemal et al., *CA: Cancer J Clin.* (2011) 61:60-90). Currently, as a first-line treatment with chemotherapy, several agents clinically approved in targeted therapies for lung cancer have ongoing developments such as bevacizumab (Avastin) (Mizuki et al., *Cancer Imaging* (2012) 12:225-36) anderlotinib (Tarceva), as well as the second generation drugs afatinib (BIBW2992) (Kim et al., *Cancer Discorv.* (2011) 1:43-51; Valerie et al., *Onco Targets and Therapy* (2013) 6:135-43) and crizotinib (Xalkori) (Ou et al., *Oncologist* (2012) 17:1351-75). However, they exhibit toxicities and have limitations due to the differences in molecular and histological profiles of lung cancers (Larsen et al., *Cancer J.* (2011) 17:512-27).

Hepatocellular carcinoma (HCC) is an aggressive cancer with the fifth highest incidence and third highest mortality rate worldwide (Jemal et al., *CA: Cancer J. Clin.* (2011) 61:60-90; Ferlay et al., *Lyon: Intl Agency for Research on Cancer* (2010).) An estimated 30,640 new cases and 21,670 cancer deaths will occur in the United States in 2013 (Cancer Facts & Figures 2013. American Cancer Society). In these patients, systemic treatments with chemotherapy, immunotherapy or hormonal therapy result in low response rates and minimal survival benefits (Rossi et al., *World J Gastrointest Oncol* (2010) 2:348-359). The current standard treatments for advanced HCC, including transarterial chemoembolization (TACE) (Liovet et al., *Hepatology* (2003) 37:429-42), adoptive immunotherapy (Takayama et al., *Lancet* (2000) 356(9232):802-807), interferon therapy (Lo et al., *Ann Surg* (2007) 245:831-42), percutaneous ethanol injection and a molecular target drug sorafenib (Rampone et al., *World J Gastroenterol* (2009) 15(26):3210-3216), showed limited impact on survival rates (Lopez et al., *Aliment Pharma-col Ther* (2006) 23(11):1535-1547). Current therapeutic approaches also do not efficiently prevent tumor multiple recurrences, which contributes to poor prognosis of the disease.

SUMMARY

Embodiments disclosed herein provide methods for treating neoplasm in a mammal, comprising intratumorally administering to the neoplasm an effective amount of a pharmaceutical composition consisting of: a hapten: and a redox agent, whereby the neoplasm is treated.

In some embodiments, the hapten is selected from the group consisting of 2,4-dinitrophenol (DNP), Benzylpenicillin, Procainamide Hydrochloride, Hydralazine Hydrochloride, Quinidine, Levamisole Hydrochloride, Inosine Pranobex, Aluminium Hydroxide, trinitrophenol (TNP), N-iodoacetyl-N'-(5-sulfonic 1-naphtyl)ethylene diamine (AED), and dinitrofluorobenzene (DNFB). In some embodiments, the redox agent is selected from the group consisting of hydrogen peroxide ($H_2O_2$), stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS), carbamide peroxide. In some embodiments, the methods comprise multiple treatments. In some embodiments, multiple haptens are used. In some embodiments, each treatment comprises intratumorally administering to the neoplasm an effective amount of a pharmaceutical composition consisting of a redox agent and a different hapten. In some embodiments, the multiple treatments are conducted at weekly intervals. In some embodiments, the multiple treatments are conducted at bi-weekly intervals. In some embodiments, the multiple treatments are conducted at monthly intervals. In some embodiments, at least 2, 3, 4, 6, or 8 treatments are conducted. In some embodiments, the hapten and the redox agent are formulated in a single composition. In some embodiments, the methods further comprise intratumorally administering to the neoplasm at least two chemotherapeutic agents. In some embodiments, the methods comprise forced distribution of the pharmaceutical composition in the neoplasm. In some embodiments, the pharmaceutical composition is administered to the neoplasm at a pressure that is about 4 AMP to about 6 AMP. In some embodiments, the pharmaceutical composition is administered to the neoplasm at a pressure that is about 5 AMP to about 6 AMP. In some embodiments, the pharmaceutical composition is distributed throughout the matrix of the whole tumor. In some embodiments, the survival rate of the patients with multiple treatments is improved in comparison to the survival rate of the patients with single treatment. In some embodiments, the mean survival of the patients with multiple treatments is improved in comparison to the mean survival of the patients with single treatment. In some embodiments, the neoplasm to be treated is selected from the group consisting of adrenal gland, anus, bile ducts, bladder, bone, breast, buccal, cervix, colon, ear, endometrium, esophagus, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, stomach, testes, thyroid, tonsil, urethra, uterus, vagina, and vulva. In some embodiments, the neoplasm to be treated is solid tumor. In some embodiments, the size of the solid tumor is larger than $10^8$ cells. In some embodiments, the size of the solid tumor is from about $5\times10^9$ to about $10^{11}$ cells. In some embodiments, the neoplasm is induced into necrosis and/or is induced into fibrosis. In some embodiments, the neoplasm is induced into fibrosis. In some embodiments, the methods comprise administering an immune response potentiator to the neoplasm. In some embodiments, the immune response potentiator is selected from the group consisting of Bacille Calmette-Guerin (BCG); *Corynebacterium Parvum; Brucella abortus* extract; glucan; levamisole; tilorone; an enzyme selected from the group consisting of *Vibrio cholera* neuramidase (VCN), Papain, β-Gal and ConA; a non-virulent Newcastle virus; and a polysaccharide selected from the group consisting of sizofuran (SPG), schizophyllan, mannan, lentinan, Su-polysaccharide (Su-Ps) and mannozym. In some embodiments, an immune response is generated against the neoplasm. In some embodiments, the immune response comprises or is a humoral and/or cellular immune response.

BRIEF DESCRIPTION OF THE DRAWINGS

FIG. 5-1: Survival curve (Kaplan-Meier). Overall survival curves and comparison of overall survival (OS) between UMIPIC and ITCT groups (P=0.0028). FIG. 5-2: Survival curve of patients between UMIPIC and ITCT with two cycles of therapies (Kaplan-Meier). FIG. 5-3: Survival curve of patients between UMIPIC and ITCT without adjuvant treatment (Kaplan-Meier).

FIG. 6 shows clinical response of UMIPIC therapy in lung cancer. FIG. 6.1: Response of UMIPIC therapy in lung tumor. The patient is a 49-year-old female diagnosed with lung cancer, adenocarcinoma, sited in the right lobe. She received a total of 8 UMIPIC injections. (A) The tumor with a diameter of 64 cm pre-treatment and (B) The cardinal of the tumor mass regressed to complete remission (CR) post-treatment. FIG. 6.2: Response of UMIPIC therapy in lung tumor. The patient is a 79-year-old male, with inoperable advanced lung cancer of squamous carcinomaat the time of diagnosis. He received a total of four UMIPIC-Therapies with adjuvant radio-therapy. (A) Tumor size was 6.7×8.1 cm pre-treatment. (B): Tumor was regressed to partial remission (PR) post treatment. FIG. 6.3: Response of UMIPIC therapy in central lung tumor. The patient is a 59-year-old female diagnosed with central lung cancer, adenocarcinoma, unresectable. She received a total of 3 UMIPIC injections. (A) The tumor with a diameter of 64 cm pre-treatment and (B) The cardinal of the tumor mass regressed to complete remission (CR) post-treatment, with cavity of fibers at primary site of central lung cancer.

FIG. 10-1 shows the abscopal effect of TCIT in a hepatocellular cancer (HCC) patient. The "abscopal effect" of immunotherapy on the HCC patient with bilateral pulmonary metastases after 11 treatments of TCIT. (A1): The primary HCC tumor mass with diameter of 13.5 cm pre-treatment. (A2): Primary HCC tumor mass with diameter of 5.2 cm post-treatment. (B1): The bilateral pulmonary metastases pre-treat. (B2): Regression of bilateral pulmonary metastases after 11 treatments of TCIT.

FIG. 10-2 shows local effect of TCIT in an HCC patient.

DETAILED DESCRIPTION OF THE PREFERRED EMBODIMENT

Figure 1:
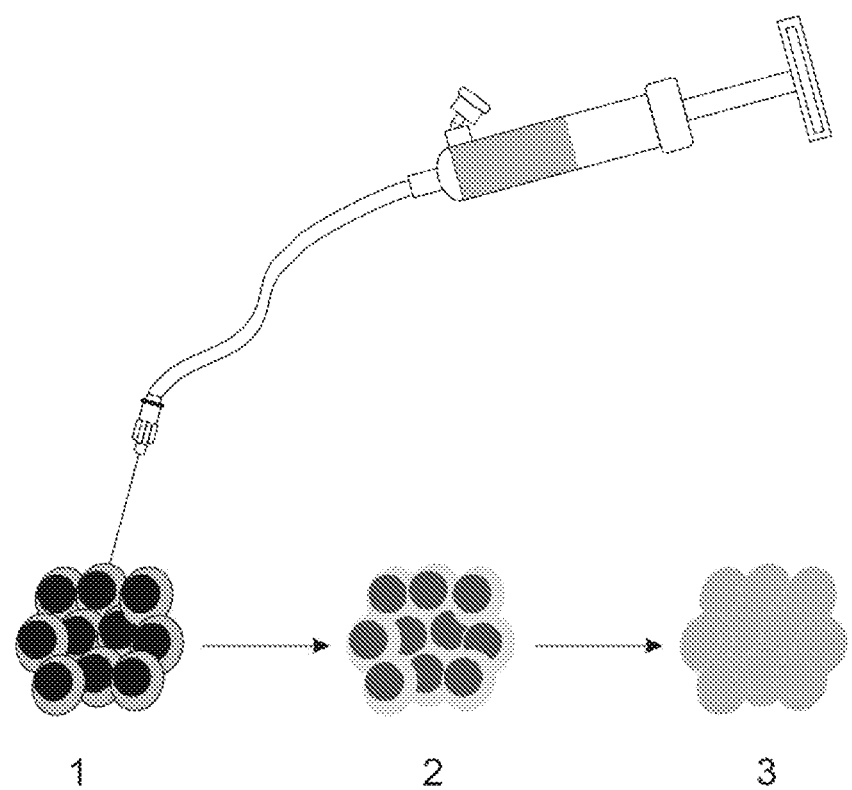
FIG. 1 shows an illustration of an exemplary embodiment of the procedure of the UMIPIC: (1) guided by CT, the needle is inserted into tumor and connected to the inflator, and introduced intratumorally with the optimal route and angle; (2) the regimens are slowly delivered into the tumor; (3) with high pressure supplied by the inflator; the solution can penetrate into the extracellular matrix of tumor and facilitate forced diffusion in tumor.

UMIPIC is a combination of therapeutic regimen for intratumoral administration into solid tumors. It contains an oxidant, cytotoxic drug and hapten, and was explored in this clinic for its personalized value based on tumor size and autologous tumor-associated antigens as self-vaccination of specific tumors. Combinatorial regimens for tumor therapeutics have been described in U.S. Pat. Nos. 6,811,788 and 8,501,243, the contents of which are hereby incorporated by reference in their entireties. UMIPIC integrates coagulation or chemotherapy simultaneously synergized with immunotherapy by percutaneous approach. In general terms, UMIPIC injected intratumorally in this clinical study can overcome the shortcomings of systematic chemotherapy and extend patient survival time based mainly on the following three principles. It also eliminates the need for a tumor-targeting agent used in some earlier anti-tumor regimens.

Although not wished to be bound by any theories or mechanisms described herein, it is the current understanding that the following targeting chemotherapy is an effective treatment for neoplasm and can induce some immunotherapic effects simultaneously using a target compound to deliver the hapten and the chemotherapeutic agent to the tissue site simultaneously, which greatly enhances the chemotherapy induced immunotherapy and has a more active contribute to the treatment of neoplasms, tumors and cancers. First, the treatment mediated by the chemical carrier means, kills at least some, in many cases more than 50% of the neoplastic cells in a target tumor. In general, the reduction of the neoplasm mass burden reduces the size of the neoplasm, beneficial to the subsequent immunotherapy. In addition, chemotherapy also results in structural changes in the cell surface, the extracellular matrix and cell lysis to release the contents of the neoplastic cells, i.e., local inflammation. This inflammatory effect, coupled with the added hapten, which is combined with the tumor-specific antigen due to neoplastic cell lysis by local chemodrugs, further generates more complex immunogens. This inflammatory area attracts various lymphocytes, such as the tumor antigen presenting cells (APCs), macrophages, dendritic cells (DCs) and activated B cells, to the area and interact with the tumor antigens, e.g., the complex tumor antigens, DNAs, RNAs and other contents released from the cell lysis. These interactions induce a tumor-specific immune response, which includes humoral, cellular and complement-mediated response. This local tumor-specific immune response is further enhanced by the presence of adjacent live neoplastic cells not initially killed by the local chemodrugs. In this way, the subsequent tumor-specific immune response augments the effect of the chemotherapy (in situ vaccination) and extends to the metastasized neoplastic sites preventing recurrence and metastasis of the neoplastic cells.

The present combinations and methods may also exert their therapeutic effects through their effects on extracellular matrix (EM) upon the carrier reach the tissue area including tumor tissue area. This combination can increase differences of extracellular matrix. In vivo, tumor cells are surrounded by the extracellular matrix such as collagen, fibronectin, proteoglycans (protein/carbohydrate), hyaluronic acid and other high molecular weight substances, it may play an anti-cancer function too. It has been shown that there are significant differences between the EM of tumor and that of normal tissues.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, an oxidation-reduction reaction refers to a reaction in which electrons are transferred from a donor to an acceptor molecule.

As used herein, an oxidizing agent (or oxidant) refers to an agent that accepts electrons in an oxidation-reduction reaction.

As used herein, a reducing agent (or reductant) refers to an agent that donates electrons in an oxidation-reduction reaction.

As used herein, hapten refers to an antibody-specific substance that cannot induce antibody formation unless bound to a carrier or molecules. Once a hapten is conjugated to a carrier/molecule, the antibody produced using the conjugate may recognize the hapten and/or the carrier/portion. The conjugate of hapten-carrier/molecule may also generate specific cellular immune response.

As used herein, an anti-neoplastic treatment refers to any treatment designed to treat the neoplasm, tumor or cancer by lessening or ameliorating its symptoms. Treatments that prevent the occurrence of neoplasm, tumor or cancer or lessen its severity are also contemplated.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, malignant, as applies to tumors, refers to primary tumors that have the capacity of metastasis with loss of both growth control and positional control.

As used herein, an anti-neoplasm agent (used interchangeably with anti-neoplastic agent, anti-tumor or anti-cancer agent) refers to any agents used in the anti-neoplasm treatment. These include any agents, that when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein. Anti-neoplastic agents include, but are not limited to, anti-angiogenic agents, alkylating agents, antimetabolite, certain natural products, platinum coordination complexes, anthracenediones, substituted ureas, methylhydrazine derivatives, adrenocortical suppressants, certain hormones and antagonists, anti-cancer polysaccharides and certain herb extracts such as Chinese herb extracts.

As used herein, anti-neoplasm agent (or anti-tumor or anti-cancer agent) or anti-neoplasm treatment does not encompass a combination comprising an oxidizing agent or a reducing agent, a protein denaturing agent; and a hapten, or use thereof for treatment, but encompasses all agents and treatment modalities known to those of skill in the art to ameliorate the symptoms in some manner of a neoplasm, tumor or cancer.

As used herein, "angiogenesis" refers to the generation of new blood vessels from parent microvessels. Angiogenesis is highly regulated by a system of angiogenic stimulators and inhibitors. Pathological angiogenesis is caused by a shift in the net balance between stimulators and inhibitors of angiogenesis, e.g., due to the overproduction of normal or aberrant forms of angiogenic mediators, or due to a relative deficiency in inhibitors of this process.

As used herein, "undesired and/or uncontrolled angiogenesis" refers to pathological angiogenesis wherein the influence of angiogenesis stimulators outweighs the influence of angiogenesis inhibitors.

As used herein, "anti-angiogenic treatment or agent" refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. As used herein, "inhibitor of an endotheliase" is not considered an "anti-angiogenic treatment or agent."

As used herein, "antisense polynucleotides" refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand.

As used herein, antibody includes antibody fragments, such as Fab fragments, which are composed of a light chain and the variable region of a heavy chain.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "a facilitating agent that facilitates conjugation between the hapten and a tumor antigen" refers to an agent that links the hapten to the tumor antigen, or any agent that facilitates such linkage. The linkage between the hapten and the tumor antigen can be covalent or non-covalent, and can be mediated by hydrophobic, polar, ionic, electrostatic or other interactions.

As used herein, "immune response" refers to alteration in the reactivity of an organism's immune system in response to an antigen; in vertebrates, this may involve antibody production, induction of cell-mediated immunity, complement activation or development of immunological tolerance.

As used herein, "immune response potentiator" refers to a substance that enhances an antigen's effect in eliciting an immune response.

As used herein, "coagulation" refers to a process of causing transformation of cells, contents therein, and extracellular matrix into a soft, semisolid or solid mass.

As used herein, "coagulation lysing agent" refers to an agent that loosens or solubilize the coagulation.

As used herein, "coagulation of neoplasm" refers to a process of causing transformation of neoplastic cells, contents therein, and extracellular matrix into a soft, semisolid or solid mass, which transformation results in death of the coagulated neoplastic cells and enhance the coagulated neoplastic cells' retention of agents administered to the neoplasm.

As used herein, the terms "a therapeutic agent", "therapeutic regimen", "radioprotectant", "chemotherapeutic" mean conventional drugs and drug therapies, including vaccines, which are known to those skilled in the art. "Radiotherapeutic" agents are well known in the art.

As used herein the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, *The Science and Practice of Pharmacy*. 20$^{th}$ ed., (Lippincott, Williams & Wilkins 2003). Except insofar as any conventional media or agent is incompatible with the active compound, such use in the compositions is contemplated.

A "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.*, 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

As used herein, the term "therapeutically effective amount" or "effective amount" refers to an amount of a therapeutic agent that when administered alone or in combination with an additional therapeutic agent to a cell, tissue, or subject is effective to prevent or ameliorate the tumor or the progression of the tumor or an associated disease associated with the tumor. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In particular, an effective amount is an amount that kills cancer cells and/or inhibits or reduces tumor progression.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, amelioration of the symptoms of a particular disorder by administration of a particular pharmaceutical composition refers to any lessening, whether permanent or temporary, lasting or transient that can be attributed to or associated with administration of the composition.

B. Methods of Treatment

Embodiments disclosed herein provide methods for treating neoplasm in a mammal, comprising intratumorally administering to the neoplasm an effective amount of a pharmaceutical composition consisting of a hapten and a redox agent, wherein the neoplasm is treated.

Tumor-associated antigens, especially the antigens modified with hapten (generated from the tumor cell lysis) elicit a tumor-specific immune response, which can encompass hormonal, cellular and complement-mediated responses. In some embodiments, the hapten may be selected from the group consisting of 2,4-dinitrophenol (DNP), Benzylpenicillin, Procainamide Hydrochloride, Hydralazine Hydrochloride, Quinidine, Levamisole Hydrochloride, Inosine Pranobex, Aluminium Hydroxide, trinitrophenol (TNP), N-iodoacetyl-N'-(5-sulfonic 1-naphtyl)ethylene diamine (AED), and dinitrofluorobenzene (DNFB).

In some embodiments, the hapten may also be selected from the group consisting of any drug useful in treating cancer, cisplatin, carboplatin, calcium folinate, vincristine, methotrexate, fluorouracil, Ara-C, cyclophosphamide, epirubicin, doxorubicin rapid dissolution, mitomycin, etoposide, bleomycin A5, etc.

In preferred embodiments, the methods disclosed herein include multiple treatments conducted at certain intervals, for example, weekly, bi-weekly, monthly, etc. The treatment intervals may vary for the same patient. For example, the treatment interval may be adjusted according to the patient's response, or lack thereof, to the previous treatment. The number of treatments is contemplated to be at least 2, at least 3, at least 4, at least 5, at least 6, at least 8, or more.

For multiple treatments, multiple haptens may be used. In some embodiments, a different hapten is used for each treatment. In some other embodiments, the same hapten may be used for more than 1 treatment. Therefore, a total of 2, 3, 4, 5, 6, 7, 8, or more haptens may be used on the same patient. The selection of hapten may depend on the patient's response, or lack thereof, to the previous treatment. It can be appreciated by one of ordinary skill in the art that a variety of combinations of haptens may be used for treating a patient. For example, in some embodiments, 4 different haptens may be used for four treatments of a patient. In some embodiments, 2,4-dinitrophenol (DNP), chemical drug as haptens, Benzylpenicillin, Procainamide Hydrochloride, Hydralazine Hydrochloride may be used for four treatments of a patient. In some embodiments, Quinidine, Levamisole Hydrochloride, Inosine Pranobex, Aluminium Hydroxide may be used for four treatments of a patient, etc.

Any oxidizing agent that is bio-tolerable can be used in the combination. In a preferred embodiment, the oxidizing agent used is hydrogen peroxide ($H_2O_2$), potassium peroxymonosulfate (oxone) (Wozniak et al., *Bioorg. Med. Chem. Lett.*, 8(19):2641-6 (1998)), D,L-S-methyllipoic acid methyl ester (Pan and Jordan, *Biochemistry*, 37(5):1357-64 (1998)), tertiary butyl hydroperoxide (Tarin et al., *Mol. Hum. Reprod.*, 2(12):895-901 (1996)), menadione (Santini et al., *Free Radic. Biol. Med.*, 20(7):915-24 (1996)), diamide (Bosin and Kasper, *J. Biochem. Toxicol.*, 7(3):139-45 (1992)), iodogen (Saha et al., *Int. J. Rad. Appl. Instrum.*, 16(4):431-3 (1989)), N-bromosuccinimide (Sinn et al., *Anal Biochem.*, 170(1):186-92 (1988)), omeprazole (Im et al., *J. Biol. Chem.*,260(8):4591-7 (1985)), or N-ethylmaleimide (Marzulli et al., *Boll. Soc. Ital. Biol. Sper.*, 61(1):121-7 (1985)). The oxidizing agents and compositions used in the method and combination include, but not limited to, hydrogen peroxide ($H_2O_2$), carbamide peroxide, stannous chloride ($SnCl_2$), stannous sulfate ($SnSO_4$) stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS).

Any reducing agent that is bio-tolerable can be used in the combination. In a preferred embodiment, the reducing agent used is hematoxylin, a hypoxic reducing agent such as a nitroimidazole, or nonnitro compound tirapazamine (SR-4233) (Zhang and Stevens, *Melanoma Res.*, 8(6):510-5 (1998)).

The oxidizing or reducing agent, and the hapten can be formulated in a single pharmaceutical composition or each can be formulated in a separate pharmaceutical composition.

In some embodiments, for each of the multiple treatments, one or more chemotherapeutic agents may be administered in addition to the hapten and redox agent. In preferred embodiments, at least two, at least three, at least four, or more chemotherapeutic agents may be included in each of the treatment. In some embodiments, for each treatment, a different combination of chemotherapeutic agents may be administered. Examples of such chemotherapeutic agents include, but are not limited to: Mechlorethamine, Cyclophosphamide, Melphalan (L-sarcolysin), Chlorambucil, Hexamethylmelanine, Thiotepa, Busulfan, Carmustine (BCNU), Lomustine (CCNU), Semustine (methyl-CCNU), Streptozocin (streptozotocin), Dacarbazine (DTIC; dimethyltriazenoi-midazole-carboxamide), Methotrexate (amethopterin), Fluorouacil (5-fluorouracil; 5-FU), Floxuridine (fluorode-oxyuridine; FUdR), Cytarabine (cytosine arabinoside), Mercaptopurine (6-mercaptopurine; 6-MP), Thioguanine (6-thioguanine; TG), Pentostatin (2'-deoxycoformycin), Vinblastine (VLB), Vincristine, Etoposide, Dactinomycin, Daunombicin, Doxorubicin, Bleomycin, Plicamycin (mithramycin), Mitomycin (mitomycin C), L-Asparaginase, Interferon-alfa, Cisplatin (cis-DDP). Carboplatin, Mitoxantrone. Hydroxyurea, Procarbazine, Mitotane (o,p'-DDD), Prednisone. Hydroxyprogesterone caproate, Medroxyprogesterone acetate, Megestrol acetate, Diethylstilbestrol, Ethinyl estradiol, Tamoxifen, Testosterone propionate. Fluoxymesterone, Flutanude. Leuprolide, etc.

In yet another preferred embodiment, the chemotherapeutic agent used is cytosine analogues such as Cytidine Arabinosyladenine (araC), Daunomycin, Doxorubicin, Methotrexate (MTX); Fluorinated pyrimidines such as 5-Fluorouracil (5-FU); Hydroxyurea; 6-mercaptopurine; plant alkaloids such as vincristine (VCR), VP-16 and vinblastine (VLB); alkylating agent such as Cyclophosphamide tumor cell lyses ide, Mesna, Melphalan, BCNU, Cisplatin, Nitrogen Mustard (HN2), Trisamine (HN3); Nonclassic alkylating agent such as Procarbazine; Bleomycin; Mitomycin C; Actinomycin D (DACT); or an enzyme such as L-Asparaginase.

The dosage of each combination can be empirically determined, but is generally the dosage normally used for treating neoplasms, tumors and cancers, and an amount sufficient to further enhance other neoplasm treatment, or sufficient when used alone to reduce or ameliorate or in some manner reduce symptoms of the neoplasms. The combinations can be packaged as kits.

The neoplasms, tumors and cancers that can be treated include, but are not limited to, the neoplasm of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm, lymph and lymph node metastases of various cancers, and malignant lymphoma. Preferably, the neoplasms, tumors and cancers to be treated are a solid tumor. The combinations are particularly effective for solid tumors, including solid tumor larger than $10^8$ cells, e.g., from about $5 \times 10^9$ to about $10^{11}$ cells but not limited to other kind of any size tumors.

In preferred embodiments, the hapten and the redox agent(s) are administered to the neoplasm via injection. For better distribution of the injected solution in tumor, the solution can be injected slowly with high pressure, e.g. up to 6 AMP, injector or syringe. For example, the solution may be injected to the tumor at a pressure that is, is about, is more than, 1 AMP, 2 AMP, 3 AMP, 4 AMP, 5 AMP, 6 AMP, or a range that is between any two of the above values. In some embodiments, the solution is injected to the tumor at a pressure that is about 1 AMP to about 3 AMP. In some embodiments, the solution is injected to the tumor at a pressure that is more than about 5 AMP. The solution can also be injected with a 15-35 gauge needle. During the injection, the tip of needle can be turned around in tumor by turning the handle of the needle. Injection doses and frequency should be adjusted according to the nature, size and location of the tumor, and the progress of the treatment. Injection channels can be prepared for better distribution of the solution in tumor prior to the actual injection using spinal needle for preinjection into the tumor before the injection of solution. Injection can also be performed under the guidance of CT, MR, ultrasound and other suitable imaging technologies. In some embodiments, the pharmaceutical composition is distributed throughout the matrix of the whole tumor.

Accordingly, the methods disclosed herein with multiple treatments may lead to improved therapeutic effect(s) in comparison to a method that has a single treatment. For example, the methods with multiple treatments may lead to survival, e.g., cancer-free survival, total survival, 6-mont survival, 1-year survival, mean survival, etc. in treated patients. In some embodiments, patients treated with multiple treatments may show an improvement in 6-month survival that is, is about, is more than, 100%, 20%, 30%, 40%, 50%, 60%, 70%, 80%, 90%, 100%, 150%, 200%, or a range that is between any two of the above values, in comparison to patients treated with a single treatment. For example, patients treated with multiple treatments may show an improvement in 6-month survival that is about 20% to about 50%, about 40% to about 80%, more than 90%, etc., in comparison to patients treated with a single treatment.

In some embodiments, patients treated with multiple treatments may show an improvement in 1-year survival that is, is about, is more than, 100%, 20%, 30%, 40%, 50%, 60%, 70%, 80%, 90%, 100%, 150%, 200%, or a range that is between any two of the above values, in comparison to patients treated with a single treatment. For example, patients treated with multiple treatments may show an improvement in 1-year survival that is about 20% to about 50%, about 40% to about 80%, more than 90%, etc., in comparison to patients treated with a single treatment.

In some embodiments, patients treated with multiple treatments may show an improvement in mean survival that is, is about, is more than, 10%, 20%, 30%, 40%, 50%, 60%, 70%, 80%, 90%, 100%, 150%, 200%, or a range that is between any two of the above values, in comparison to patients treated with a single treatment. For example, patients treated with multiple treatments may show an improvement in mean survival that is about 20% to about 50%, about 40% to about 80%, more than 90%, etc., in comparison to patients treated with a single treatment.

Accordingly, the methods disclosed herein with multiple haptens may lead to improved therapeutic effect(s) in comparison to a method that uses a single hapten. For example, the methods with multiple haptens may lead to survival, e.g., cancer-free survival, total survival, 6-mont survival, 1-year survival, mean survival, etc. in treated patients. In some embodiments, patients treated with multiple haptens may show an improvement in 6-month survival that is, is about, is more than, 10%, 20%, 30%, 40%, 50%, 60%, 70%, 80%, 90%, 100%, 150%, 200%, or a range that is between any two of the above values, in comparison to patients treated with a single hapten. For example, patients treated with multiple haptens may show an improvement in 6-month survival that is about 20% to about 50%, about 40% to about 80%, more than 90%, etc., in comparison to patients treated with a single hapten.

In some embodiments, patients treated with multiple haptens may show an improvement in 1-year survival that is, is about, is more than, 10%, 20%, 30%, 40%, 50%, 60%, 70%, 80%, 90%, 100%, 150%, 200%, or a range that is between any two of the above values, in comparison to patients treated with a single hapten. For example, patients treated with multiple haptens may show an improvement in 1-year survival that is about 20% to about 50%, about 40% to about 80%, more than 90%, etc., in comparison to patients treated with a single hapten.

In some embodiments, patients treated with multiple haptens may show an improvement in mean survival that is, is about, is more than, 100%, 20%, 30%, 40%, 50%, 60%, 70%, 80%, 90%, 100%, 150%, 200%, or a range that is between any two of the above values, in comparison to patients treated with a single hapten. For example, patients treated with multiple haptens may show an improvement in mean survival that is about 20% to about 50%, about 40% to about 80%, more than 90%, etc., in comparison to patients treated with a single hapten.

In another specific embodiment, the combination further comprises an immune response potentiator to enhance the autologous tumor-specific immune response. Preferably, the immune response potentiator used is Bacille Calmette-Guerin (BCG) (*Ratliff Eur: Urol.*, 2:17-21 (1992)), *Coryne-* bacterium Parvum (Lillehoj et al., *Avian Dis.*, 37(3):731-40 (1993)), *Brucella abortus* extract, glucan, levamisole, tilorone, an enzyme, a non-virulent virus, polysaccharides, or herb extracts such as Chinese herb extracts. More preferably, the enzyme used is *Vibrio cholera* neuraminidase (VCN) (Seiler and Sedlacek, *Recent Results Cancer Res.*, 75:53-60 (1980)), Papain (Helting and Nau, Acta *Pathol. Microbiol Immunol. Scand.*, 92(1):59-63 (1984); and Hess, *Eur. J Immunol.*, 6(3):188-93 (1976)), 3-Gal or ConA. Also more preferably, the non-virulent virus used is a non-virulent Newcastle virus (Meulemans et al., *Vet. Rec.*, 143(11):300-3 (1998); and Adams,*Poult. Sci.*, 49(1):229-33 (1970)). Furthermore preferably, the polysaccharides used are anti-tumor polysaccharide from the mycelium of liquid-cultured *Agaricus* blazei mill (preliminarily glucomannan with a main chain of $\beta$-1,2-linked D-mannopyranosyl residues and $\beta$-D-glucopyranosyl-3-O-beta-D-glucopyranosyl residues as a side chain (Mizuno et al., *Biochem. Mol. Biol.* Int., 47(4): 707-14 (1999)); anti-tumor polysaccharide preparation from *Flammulina velutipes* (The backbones of the polysaccharide is mainly composed of $\beta$-(1>3)-D-linked glucose and its molecular weight was estimated to be about 200 kD) (Leung et al., *Immunopharmacology*, 35(3):255-63 (1997)); sizofiran (SPG) (Tanji et al., *Yakugakul Zasshi*, 110(11):869-75 (1990)); schizophyllan (Sakagami et al., *Biochem. Biophys. Res. Commun.*, 155(2):650-5 (1988)); mannan (Gavrilenko et al., *Vopr. Onkol.*, 29(4):67-70 (1983)); lentinan (Haba et al., *Int. J. Cancer*, 18(1):93-104 (1976)); Su-polysaccharide (Su-Ps) (Kumazawa et al., *Gan To Kagakla Ryoho*, 14(12): 3329-35 (1987)); or mannozym (Zastrow, *Padiatr. Grenzgeb.*, 24(3):229-36 (1985)).

EXAMPLES

The following examples are offered to illustrate but not to limit the invention.

1 In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1

Hapten-Enhanced UMIPIC-Therapy in Advanced Pancreatic Cancer by Percutaneous Intratumoral Drug Delivery Under CT Guidance The concept of intratumoral drug delivery has been known for several decades (Goldberg et al., *J. Pharm Pharmacol* 2002, 54(2):159-80). Some successful examples have clearly shown the clinical feasibility of such treatment options, with significant reduction in both toxicity and tumor growth, but not in pancreatic cancer patients. Pancreatic cancer is located in a crucial organ surrounded by vital tissues and organs such as the duodenum, gallbladder, portal vein and aorta. Tumor invasion of these organs by pancreatic cancer is most common and could lead to unresectibility.

In advanced pancreatic cancer patients we compared the clinical effectiveness of hapten-enhanced chemoimmunotherapy by ultra-minimum incision personalized intratumoral chemoimmunotherapy (UMIPIC) with intratumoral chemotherapy (ITCT). We then analyzed the role of hapten as an immune booster.

Our data suggests that UMIPIC offers an ideal percutaneous intratumoral approach for chemical de-bulking of advanced pancreatic tumors (the hapten plays an important role in prolonging patients' survival time).

The article herein describes the results from 92 pancreatic cancer patients treated by UMIPIC and ITCT and the data was not reported previously since the combination with double chemotherapeutic drugs and oxidant with or without hapten as comparing study in treatments of pancreatic cancer is still undergoing in clinical research. Now the data using single drug and oxidant with or without hapten in the study of pancreatic cancer treatment were collected and analyzed. In addition to innovations in sustained drug release, we studied UMIPIC-therapy to possibly provide a new option for clinical effectiveness of hapten-enhanced chemoimmunotherapy (a likely cancer autologous vaccine) compared with ITCT. We further analyzed the role of hapten's role as an immune booster.

Materials and Methods

Patient Selection:

The patients selected were diagnosed with at least one solid pancreatic cancer tumor at least 1.5 cm in diameter, confirmed by CT imaging, biopsy and pathologic examination to be malignant. Pancreatic cancer patients with locally advanced and/or metastatic tumor(s) were treated with UMIPIC-therapy or intratumoral chemotherapy (ITCT).

The study was conducted with a total of 92 cases. All patients signed the informed consent form and randomized into groups of UMIPIC and ITCT for therapy, the hospital Ethics Committee approved the study.

At the end of follow-up a total of 83 patients remained (9 cases did not complete the study). UMIPIC-therapy group (n=57) had 33 with response data and 25 with survival data. The ITCT group (n=26) had 14 with response data and 20 with survival data. The 26 patients remaining in the ITCT group were treated with an oxidant and cytotoxic drug without hapten, and the 57 patients remaining in the UMIPIC-Therapy group were treated with an oxidant and a cytotoxic drug plus hapten [Table 1]. The baseline characteristics of the patients were well balanced between the two groups with no significantly difference (P>0.05).

TABLE 1

Patient Baseline Characteristics

|  | ITCT | | UMIPIC | |
| --- | --- | --- | --- | --- |
|  | N | % | N | % |
| Enrolled patients | 26 | 31.2 | 57 | 68.6 |
| Sex    Male | 14 | 53.8 | 32 | 56.2 |
|        Female | 12 | 46.1 | 25 | 43.8 |
| Age rang |  | 35-68 |  | 28-72 |
| Diabetes | 11 | 42.3 | 7 | 12.2 |
| Cigarette smoking | 6 | 23.1 | 21 | 36.8 |
| Alcohol intake | 5 | 19.2 | 20 | 35.0 |
| Stage of disease |  |  |  |  |
| Stage I | 0 |  | 0 |  |
| Stage II | 5 | 19.2 | 5 | 8.8 |
| Stage III | 3 | 11.5 | 4 | 7.0 |
| Stage IV | 12 | 46.1 | 14 | 24.6 |
| Cytological diagnosed Cancer | 6 | 23.0 | 34 | 59.6 |
| Tumor size |  |  |  |  |
| <2 cm | 0 |  | 1 | 1.7 |
| 2-5 cm | 16 | 61.5 | 39 | 68.4 |
| >5 cm | 10 | 38.4 | 17 | 29.8 |
| Previous treatment |  |  |  |  |
| Prior chemotherapy | 6 | 23.0 | 19 | 33.3 |
| Prior adjuvant therapy | 11 | 42.3 | 34 | 59.6 |

TABLE 1-continued

Patient Baseline Characteristics

| | ITCT | | UMIPIC | |
|---|---|---|---|---|
| | N | % | N | % |
| Disease status | | | | |
| Locally advanced | 9 | 34.6 | 20 | 35.1 |
| Metastatic disease | 11 | 42.3 | 21 | 36.8 |

Indication and Contraindications for UMIPIC and ITCT

All patients with pancreatic cancer were the indication for these therapies of UMIPIC and ITCT exception follow contraindication. Contraindications for treatment with UMIPIC and ITCT were poor performance status (Karnofsky status≤70%), nutritional impairment, presence of marked ascites, high serum total bilirubin level [>3 mg/dL (51.3 µmol/L)], and renal failure [serum creatinine level>2 mg/dL (176.8 µmol/L)]. Partial or complete thrombosis of the main portal vein was a further exclusion criterion for the procedure, as were cardiovascular or respiratory failure.

Preparation of Agents

As pancreatic tissue is quite fragile, a concern for injections is bleeding, which limits their application. Fine needle biopsy is performed in clinical practice for diagnosis and evaluation of treatment for pancreatic organs, requiring a fine needle with sharp tip. Both the 25 gauge spinal needles and the inflators (inflation device, 30 atm/bar) were purchased from Merit-Medical, South Jordan, Utah. The UMIPIC and ITCT solutions were freshly prepared before each injection. UMIPIC contains clinically approved agents (an oxidant, a cytotoxic drug Ara-C, and hapten) for percutaneous intratumoral delivery, ITCT contains a clinically approved oxidant with the cytotoxic drug Ara-C.

Treatment Design

Routine examination of cardiopulmonary function and peripheral complete blood count were done to rule out liver and/or pancreas puncturing or related contraindications. Patients with pancreatitis, intestinal obstruction and other heavy infections were not allowed to receive this therapy. Prior to UMIPIC-Therapy the patients were asked to fast without water intake for 14 hours pre-treatment in order to avoid side effects and infections. In order to control pain during the therapy, 50 mg of morphine was injected im at least 30 minutes pretreatment. The skin was cleansed and local anesthesia performed in the area of injection.

Figures 1, 2A:
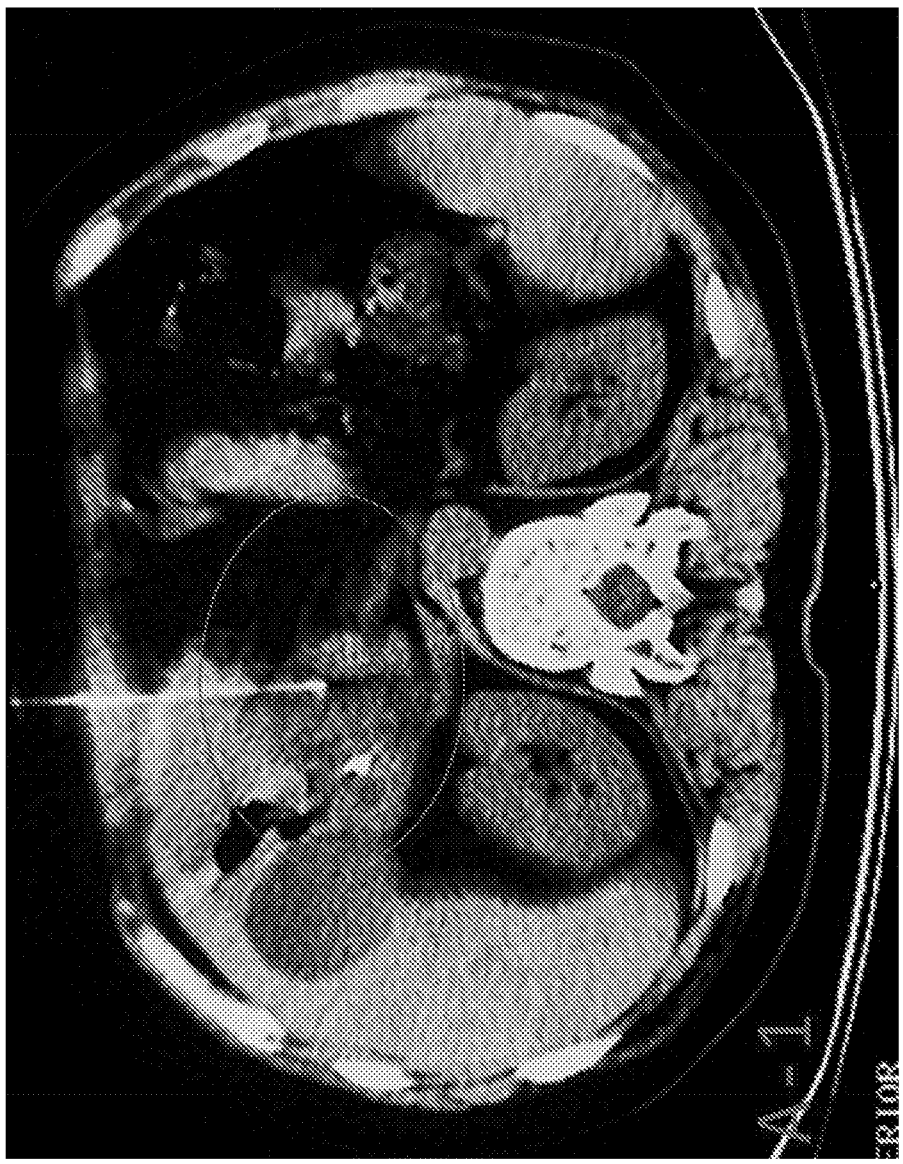
Figures 2, 2A:
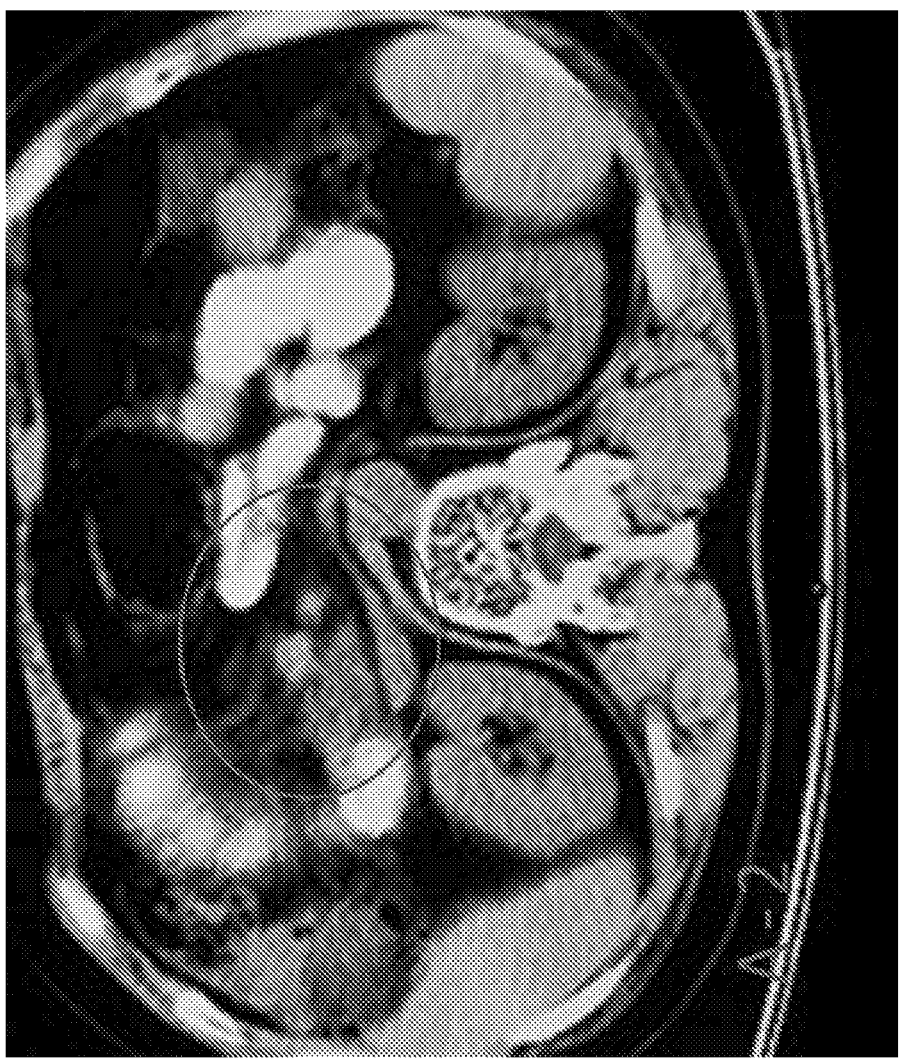
FIG. 2 shows the CT result of the pancreatic patient treated by UMIPIC-Therapy. A: CT imaging during UMPIC-Therapy and at follow up visits (6 months and 2 year). A-1: During of the operation, CT imaging showed the needle in the tumor. A-2: Six months after treatment, CT showed changes in density of CT value in tumor area and indicated partial remission. A-3: Two year after treatment, CT imaging showed complete remission. This is a 58 year old patient, Mrs. Fan, Female, diagnosed with pancreatic cancer in December 2006 and laporostomy checked the pancreatic tumor, unresectability was zero as the tumor invasion included surrounding tissue. Biopsy was performed and pathology proved a pancreatic adenocarcinoma. In the same month, the patient went to our hospital and was treated with the UMIPIC-Therapy for 5 cycles of intratumoral injections. After being reexamined in 2009 and 2014, the patient has shown to be in stable condition with complete regression of tumor mass. Currently she is alive (more than 8 years of survival time). B: CT imaging showed localized tip of needle and distribution of drugs during UMIPIC-Therapy. B-1: CT imaging localized the tip of needle in tumor for injection. B-2: CT imaging showed the distribution of drugs within tumor of pancreatic cancer right after UMPIC-Therapy. This CT imaging showed that CT guided the therapy by showing the tip of needle and showed the drugs distribution in tumor by measuring the CT value changes at a point or area of tumor, it showed that the combination solution has reached the edge of tumor. C: After one cycle of UMIPIC-Therapy, it resulted in PR and repeated three more therapies to maintain patient's tumor in PR C-1: First time of UMIPIC-Therapy, CT (C-1-1) showed the tip of needle in tumor during treatment; after treatment, CT (C-1-2) showed density changes in value in tumor and indicated the distribution of drugs in the tumor. C-2: Three months from first cycle of UMIPIC-Therapy, one more therapy was provided. CT(C-2-1) showed the tip of needle in tumor. C-3: Nine months from first therapy, tumor still in partial remission, one more treatment was provided again, CT (C-3-1 and C-3-2) showed the tip of needle in tumor during of therapy and CT (C-3-3) showed the density changes in CT value in tumor after injection, and indicated that the tumor maintains in partial remission. C-4: Thirteen months later from first therapy, tumor still in partial remission, r one more treatment was provided, CT(C-4-1) showed the tip of needle in tumor during of therapy and CT (C-4-2) showed the density changes in CT value in tumor after injection, tumor maintains in partial remission, and tumor became hard like stone due to strong fibrosis in tumor, no more therapy needed for this patient again, now the patient is in very good condition and her tumor maintains in partial remission. There was a 47 year old patient, male, and was diagnosed in July, 2012 as pancreatic cancer by PET/CT, biopsy of cytology demonstrated adenocarcinoma, CA199: 67.62 ku/l, and he had UMIPIC-Therapy for first cycle therapy from 20, Jul., 2012 to 9, Oct., 2012, and went back to hospital and received nine UMIPIC-Therapy, he was followed up to two years and his tumor is in partial remission and he live normally.

The spinal needle was inserted into the tumor under CT guidance. After insertion the core was taken out of the needle (which was connected to the inflator used as a high pressure syringe), then the injection performed (FIG. 1). UMIPIC and ITCT have the same therapeutic procedure, which is minimally invasive. UMIPIC-Therapy or ITCT was delivered by a spinal needle inserted into the tumor and connected with the inflator for injection under pressure (at the level of atmospheric pressure) to obtain full distribution of clinically approved regimens in the tumor. Ultrasound or CT (Picker IQ, Phillips Healthcare, Bothell Wash.) guidance was used for scanning and monitoring of the density changes at a point or area of interest in the pancreatic tumor (FIG. 2-B). Special attention was paid to monitoring the CT value changes in the margins of surrounding tumor to ensure full distribution of drugs to the edge of the tumor (FIG. 2-B, C). Since the combination is composed of water-soluble drugs with higher pressure for injection into the tumor mass, it is different from oil-drug emulsion which is sticky and hard to distribute in tumors. The combination of drugs in UMIPIC and ITCT could penetrate into the full matrix of the tumor, even into tumor cells, with sustained release in the tumor for an extended time with the help of an oxidant (Qiong et al., *J Shandong Univ* (2007) 45:988-992). The average time of the procedure took approximately 30-45 minutes, however if the tumor was difficult to penetrate a repeat CT would be needed for monitoring. The volume of the injection was calculated based on the diameter of the tumor $(D^r) \times 2$ for 1-5 cm of tumor, and $(D^r) \times 1.5$ for 6 cm of tumor or more. Good Practice, the key for each therapy, should be based on this calculation to deliver enough dosage into the tumors.

The size of the tumor (tumor mass) is closely re-examined by CT Scanning once a week for 3 weeks, the treatment is repeated each week. Three treatments in total included the initial treatment as one cycle of UMIPIC and ITCT. If the tumor size is not stabilized, becoming smaller after 8-9 weeks when the tumor was re-examined, additional injections were added to maintain better efficacy. Distant tumors were treated the same as primary pancreatic cancer tumors if the tumor size was larger than 2 cm in other organs, such as liver or abdomen, as determined by CT or ultrasound.

Patients are closely monitored for 2 day pos-treatment, significant systematic or local adverse effects needed to be evaluated.

Assessment

The response to treatment in the solid tumor's effect was evaluated as per evaluation criterion of EROTC (European Organization for Research and Treatment of Cancer) and RECIST (NCI, US and Canada) in October 1998 (Duffaud et al., *Bull Cancer* (2000) 87(12):881-886). All case report forms (CRF) were filled by treating physicians from hospitals.

Statistical Analysis

The statistical analysis was done by a medical college. Overall survival (OS) was defined as the duration from the first treatment to the date of death, plotted according to the Kaplan-Meier method. Comparisons of effective rates were calculated with the Chi-square test. Statistical analysis was done with SPSS 17.0 statistical software and a P value of <0.05 was considered statistically significant.

Results

Efficacy Evaluation

The therapeutic effects were analyzed in 47 patients [Table. 2]. The response rate [complete remission (CR)+ partial remission (PR)/total patients] was 12.12% and 21.43%. Benefit rate [complete remission (CR)+ partial remission (PR)+ stable disease (SD)/total patients] was 87.9% and 92.9% in the UMIPIC-therapy and ITCT groups, respectively. There was no statistically significant difference between the two groups in response rate and benefit rate (Tables 2, 3). This was likely due to inflammatory response induced by coagulation (or interaction with the malignant cells) and the extremely high concentration of the cytotoxic drug locally injected. [6.7] Most tumors include distant tumors found in stable condition.

TABLE 2

Comparison of therapeutic effect between UMIPIC and ITCT groups

| Groups | N | CR | PR | SD | PD | Response rate/% | Benefit rate/% |
|---|---|---|---|---|---|---|---|
| ITCT | 14 | 0 | 3 | 10 | 1 | 21.43 | 92.86 |
| UMPIC | 33 | 0 | 4 | 25 | 4 | 12.12 | 87.88 |

TABLE 3

Comparison of therapeutic effect between UMIPIC and ITCT groups

| Groups | Response rate % | Chi square | P value | Benefit Rate/% | Chi square | P value |
|---|---|---|---|---|---|---|
| UMIPIC | 12.12 | 0.138 | >0.05 | 87.88 | 1.211 | >0.05 |
| ITCT | 21.43 | | | 92.86 | | |

UMIPIC-therapy demonstrated comparable efficacy with first line treatments, and showed significantly longer overall survival (one-year OS 28% with UMIPIC, 5% with ITCT) with minimal disruption of quality of life and clinical benefits rate to 87.9%. This result is relatively promising compared to results reported in other studies. In this study one patient with pancreatic cancer was found with partial remission (FIG. 2-A1, FIG. B), but two years after the first cycle of UMIPIC treatment, partial remission (PR) was found changed to complete remission (CR) (FIG. 2-A2-3). Partial remission and tumor stabilization were found in most patients including distant tumors (FIG. 2-C, D). The UMIPIC group had an additional 1.5 months of median survival months compared with the ITCT group with significant difference.

Figures 2, 2A, 3:
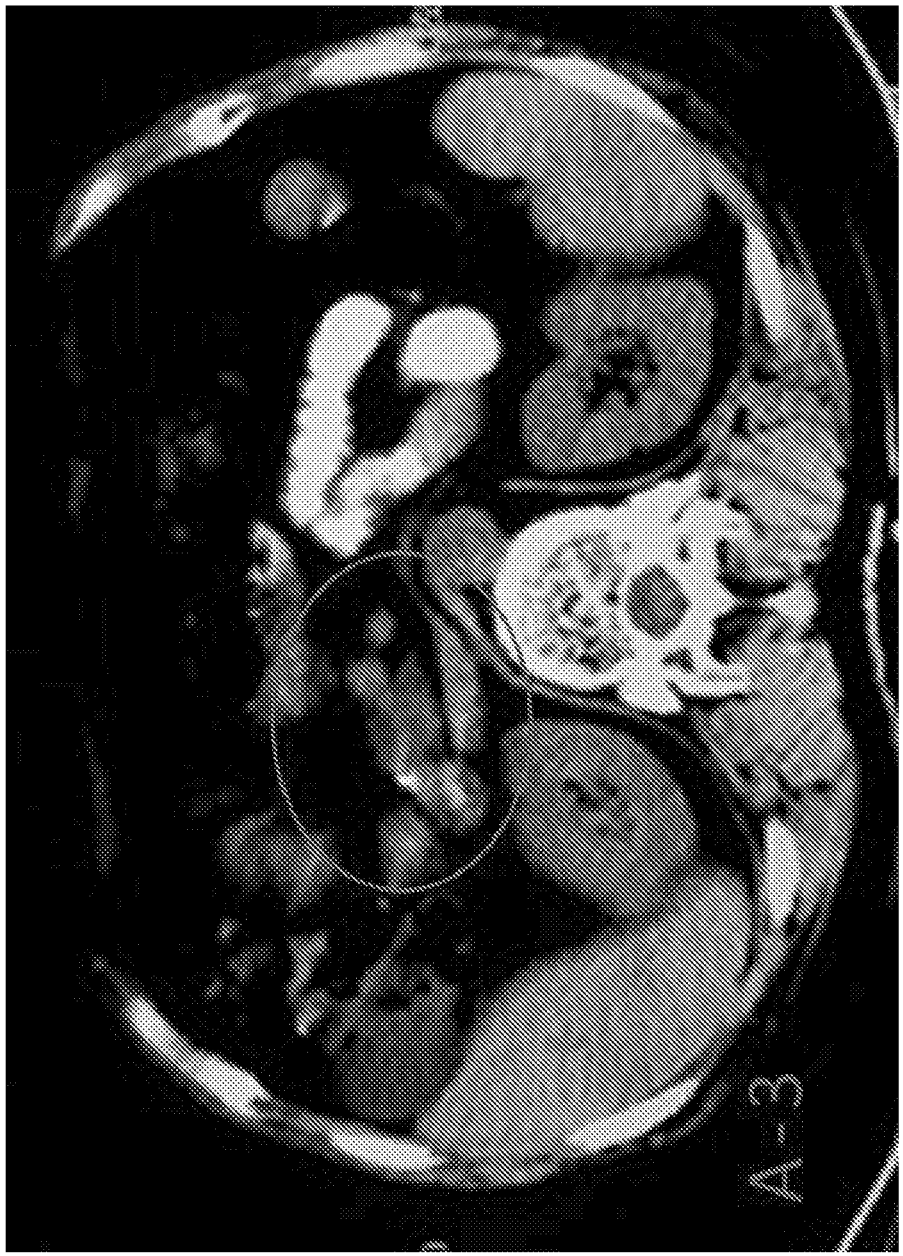
FIG. 3 shows a comparison of survival rate between UMIPIC-Therapy and ITCT Therapy.
Figures 1, 2B:
Figures 2, 2B:
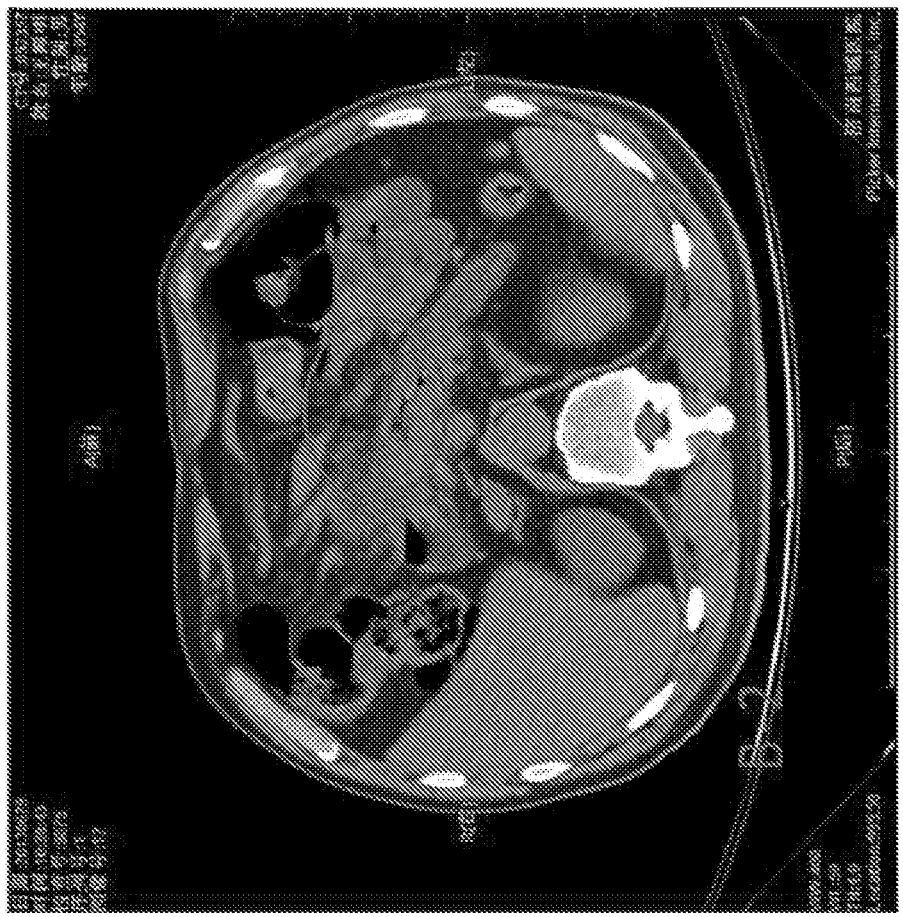
Figures 1, 2C:
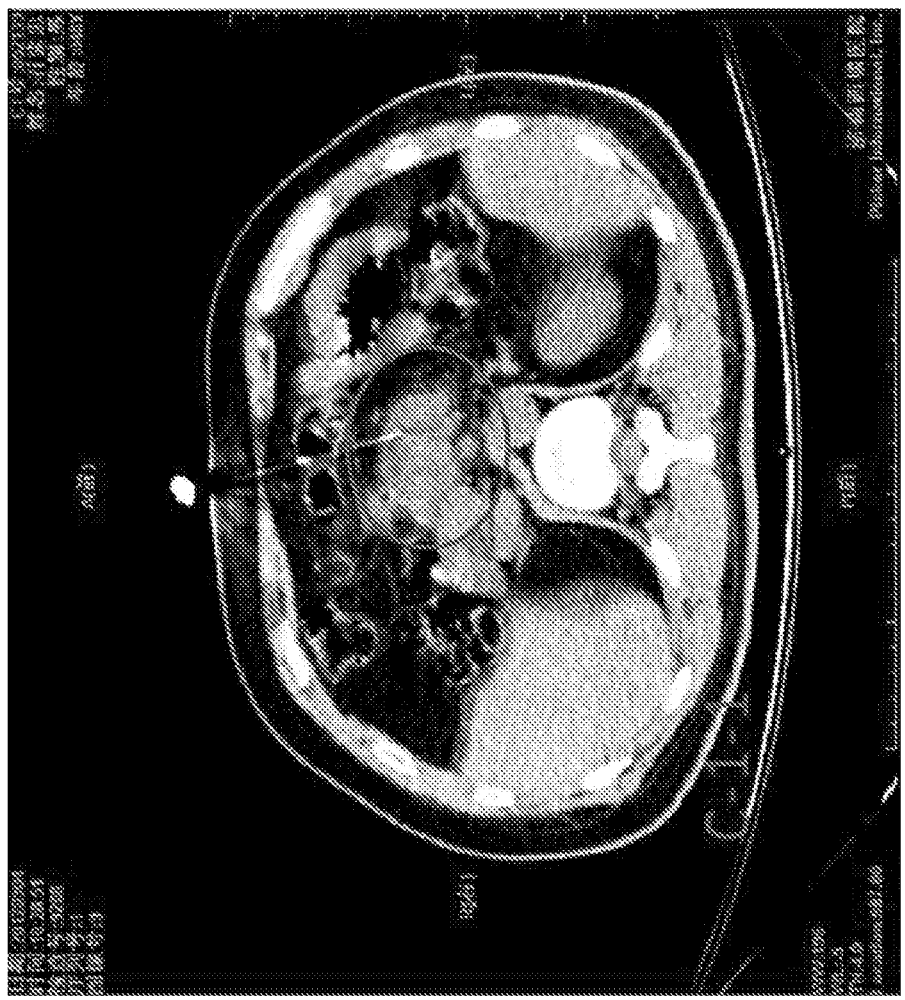
Figures 1, 2, 2C:
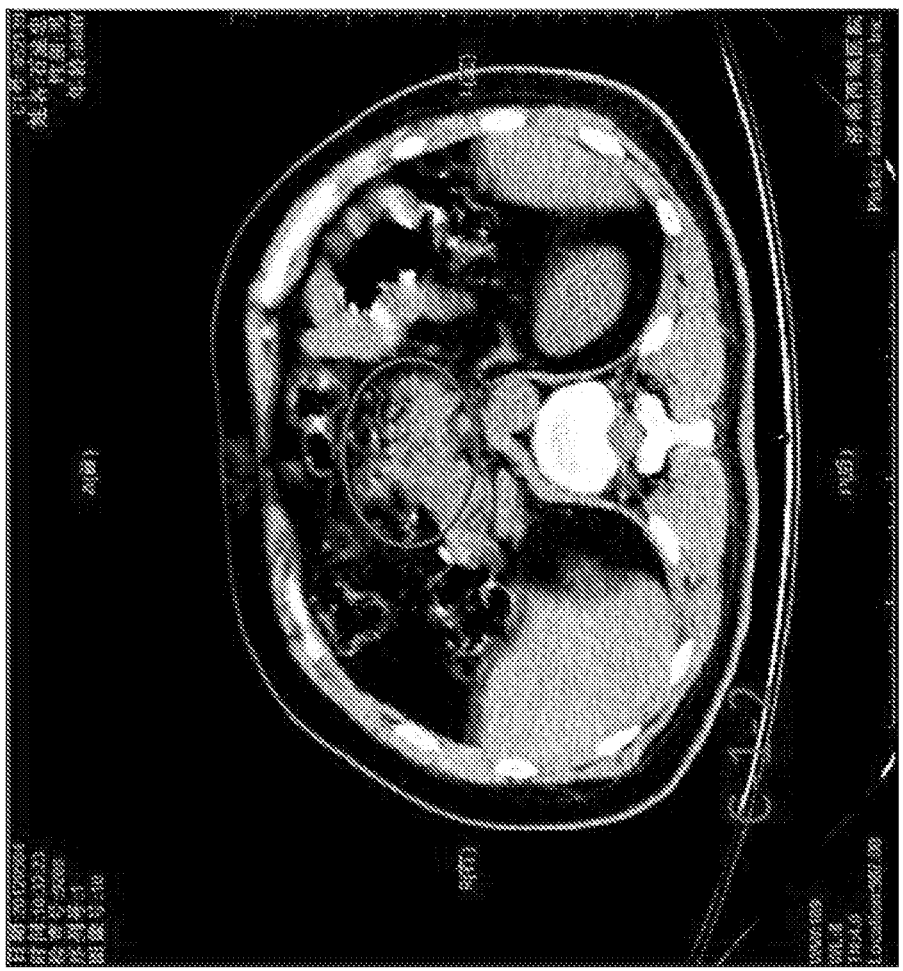
Figures 1, 2, 2C:
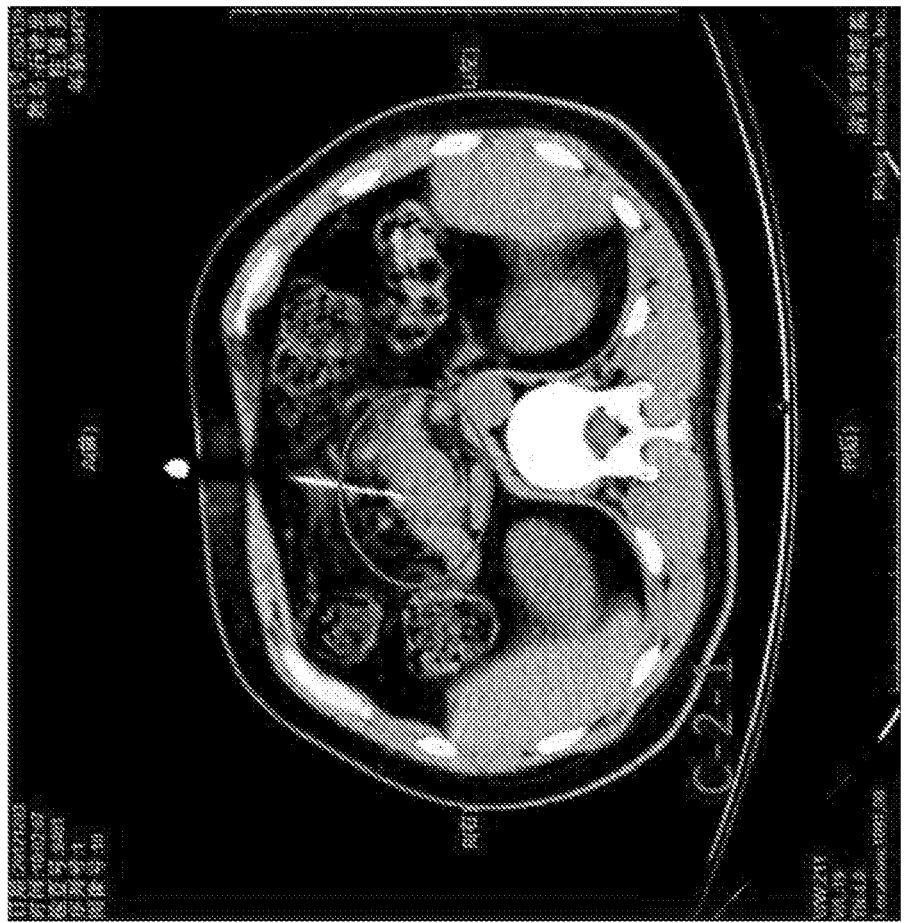
Figures 1, 2, 2C, 3:
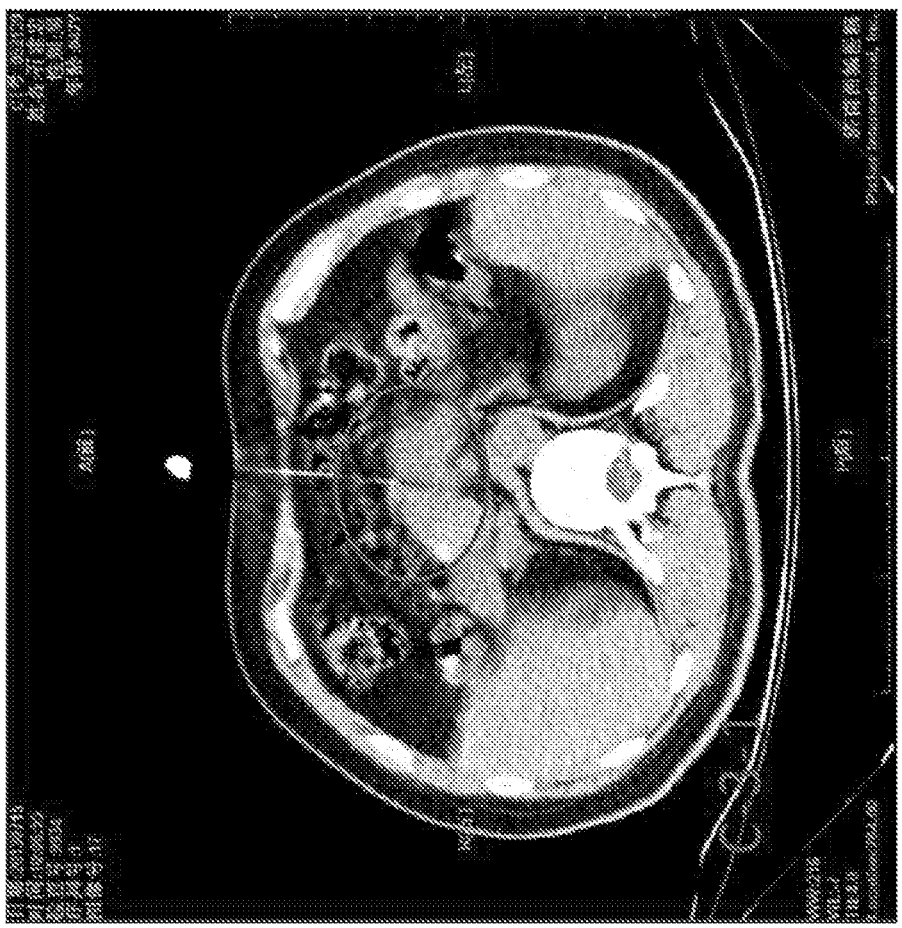
Figures 2, 2C, 3:
Figures 2, 2C, 3:
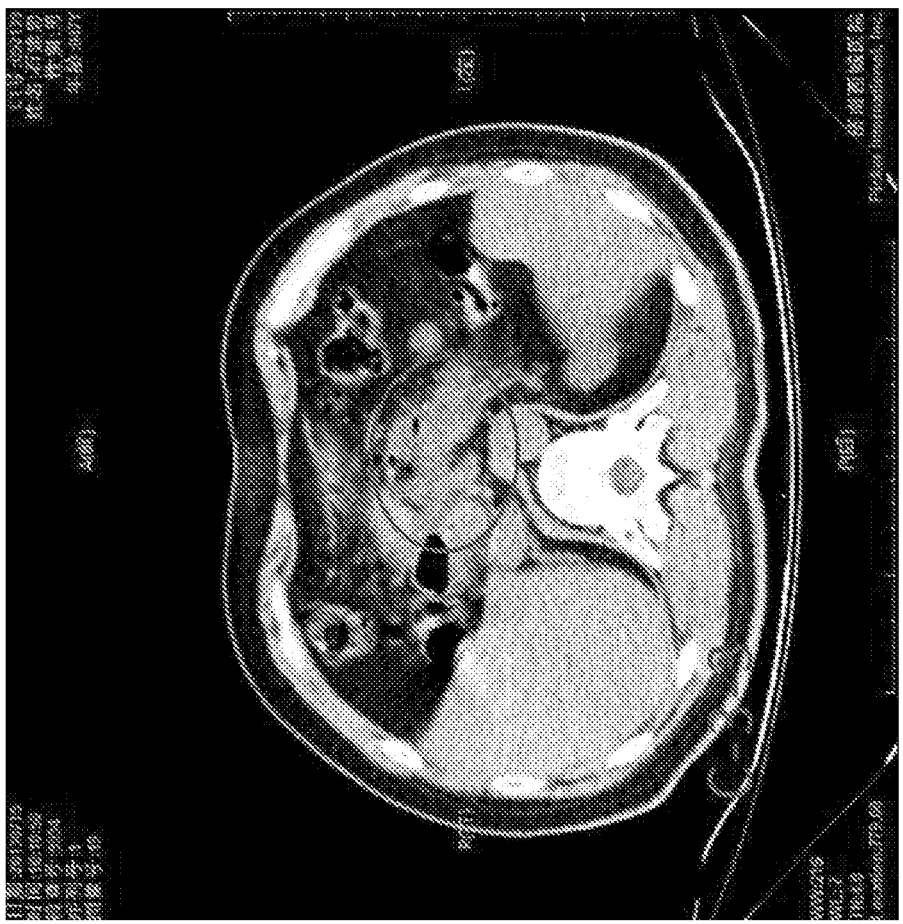
Figures 1, 2, 2C, 3, 4:
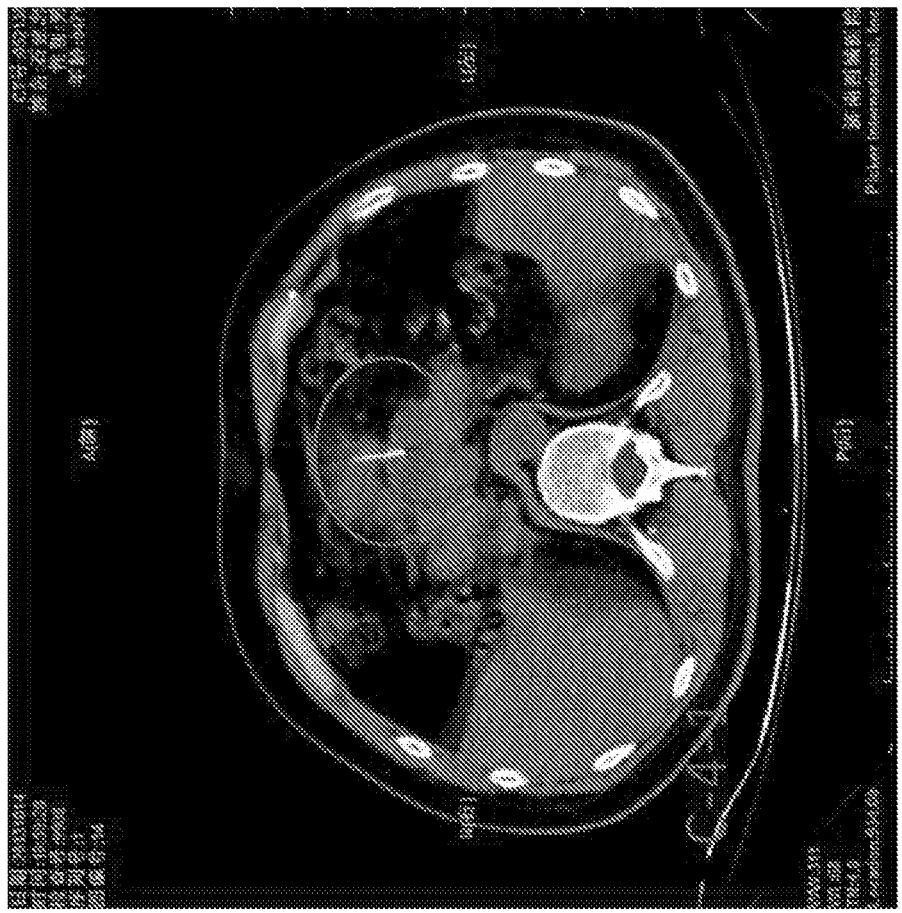
FIG. 4 shows a comparison of expression of tumor fibrosis between UMIPIC-Therapy and ITCT Therapy. A: In control group of ITCT, after 7 days of treatment, tumor was resected to obtain pathological sections for specific staining including elastic fiber staining (A1), reticular fiber staining (A2) and collagen staining (A3), less expression of the three fibers in tumor were induced by single cytotoxic drug ARA-C. B: In test group of UMIPIC, after 7 days of treatment, tumor was resected to obtain pathological sections for specific staining including elastic fiber staining (B1), reticular fiber staining (B2) and collagen staining (B3), higher expression of the three fibers in tumor were induced by cytotoxic drug ARA-C with hapten, which could limit the tumor growth or destroy of environmental condition for tumor cell growth. A1 and B1 represented the elastic fiber stain in tumor tissue (×200); A2 and B2 represented the reticular fiber stain in tumor tissue (×200); A3 and B3 represented the collagen fiber stain in tumor tissue (×200).
Figures 2, 2C, 3, 4:
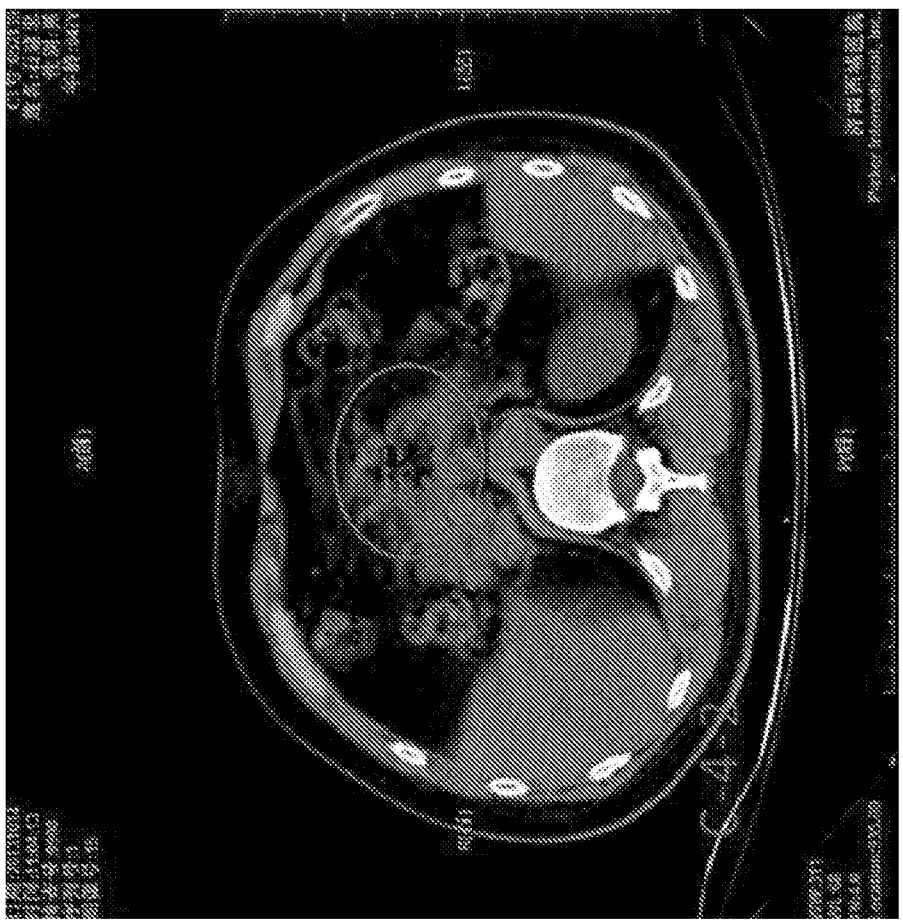
Figure 3:
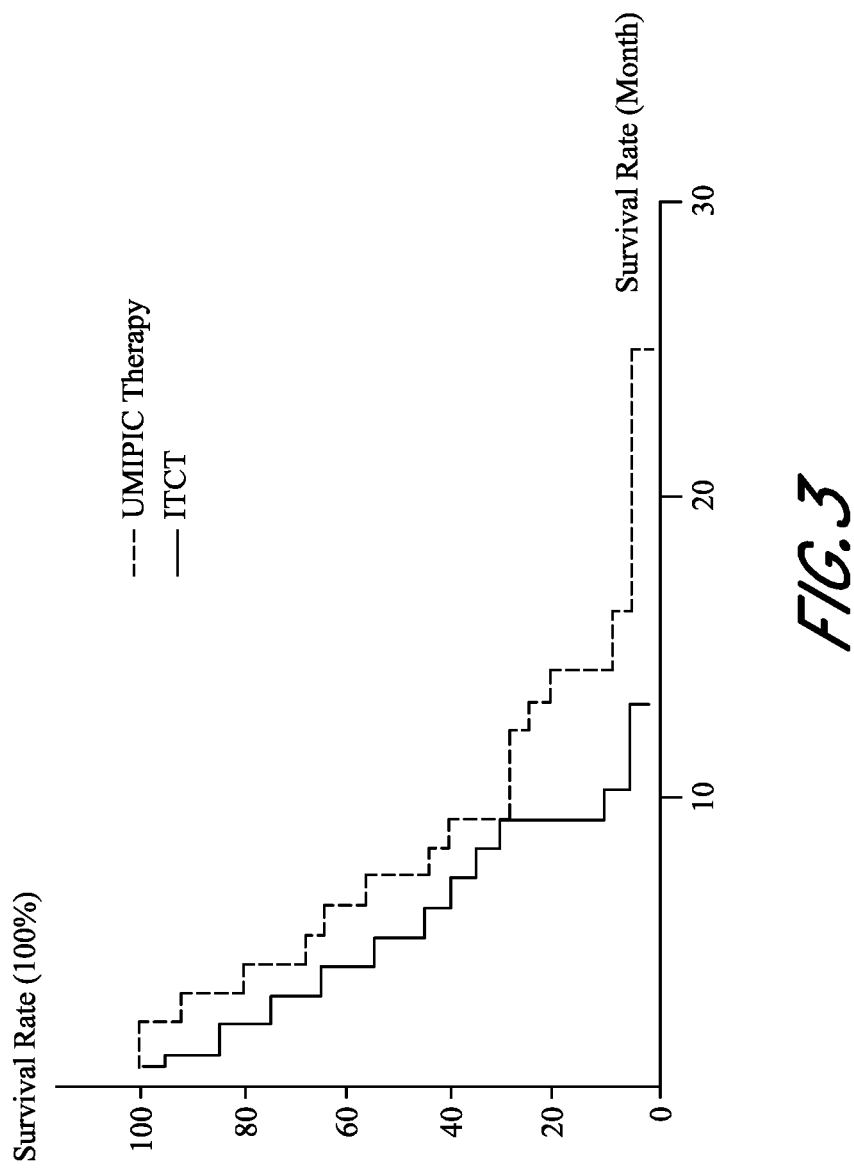
Figures 1, 4A:
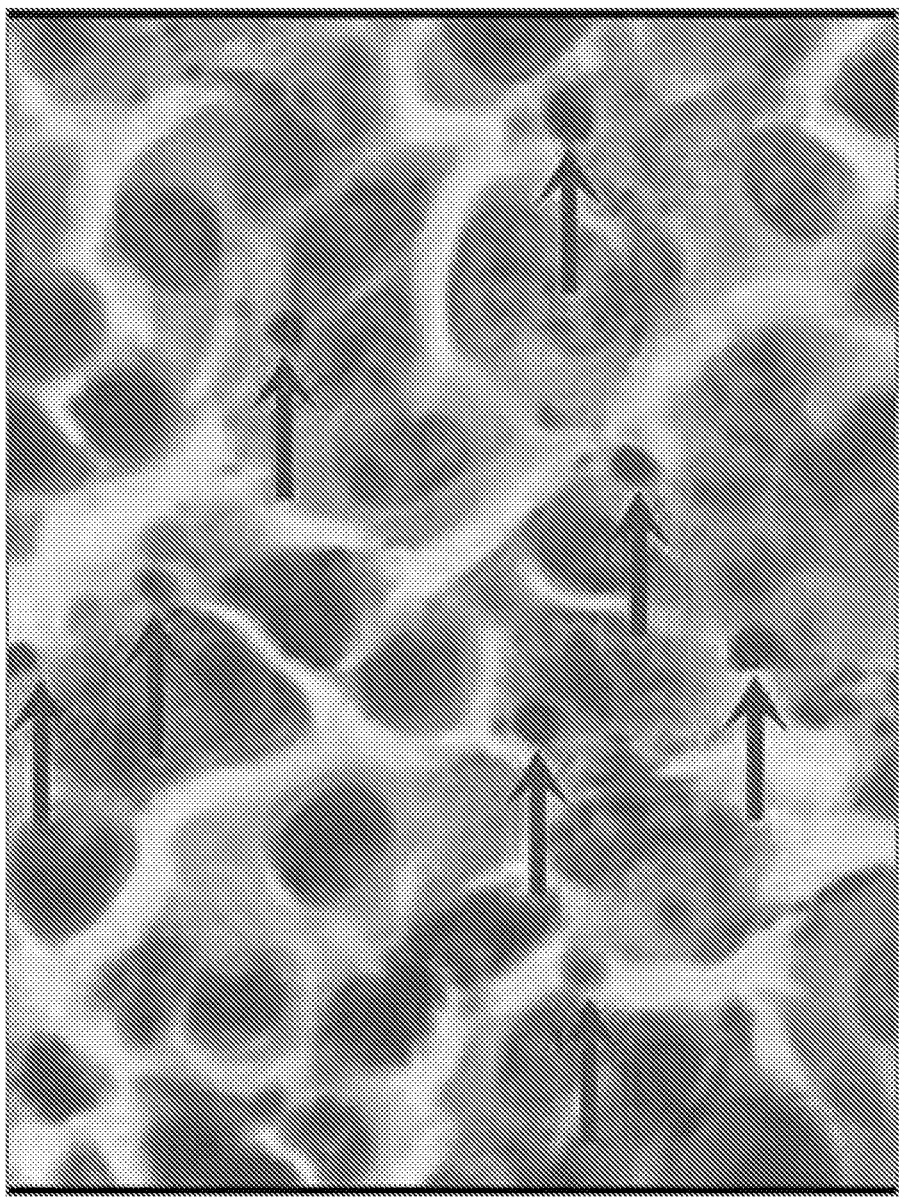
Figures 2, 4A:
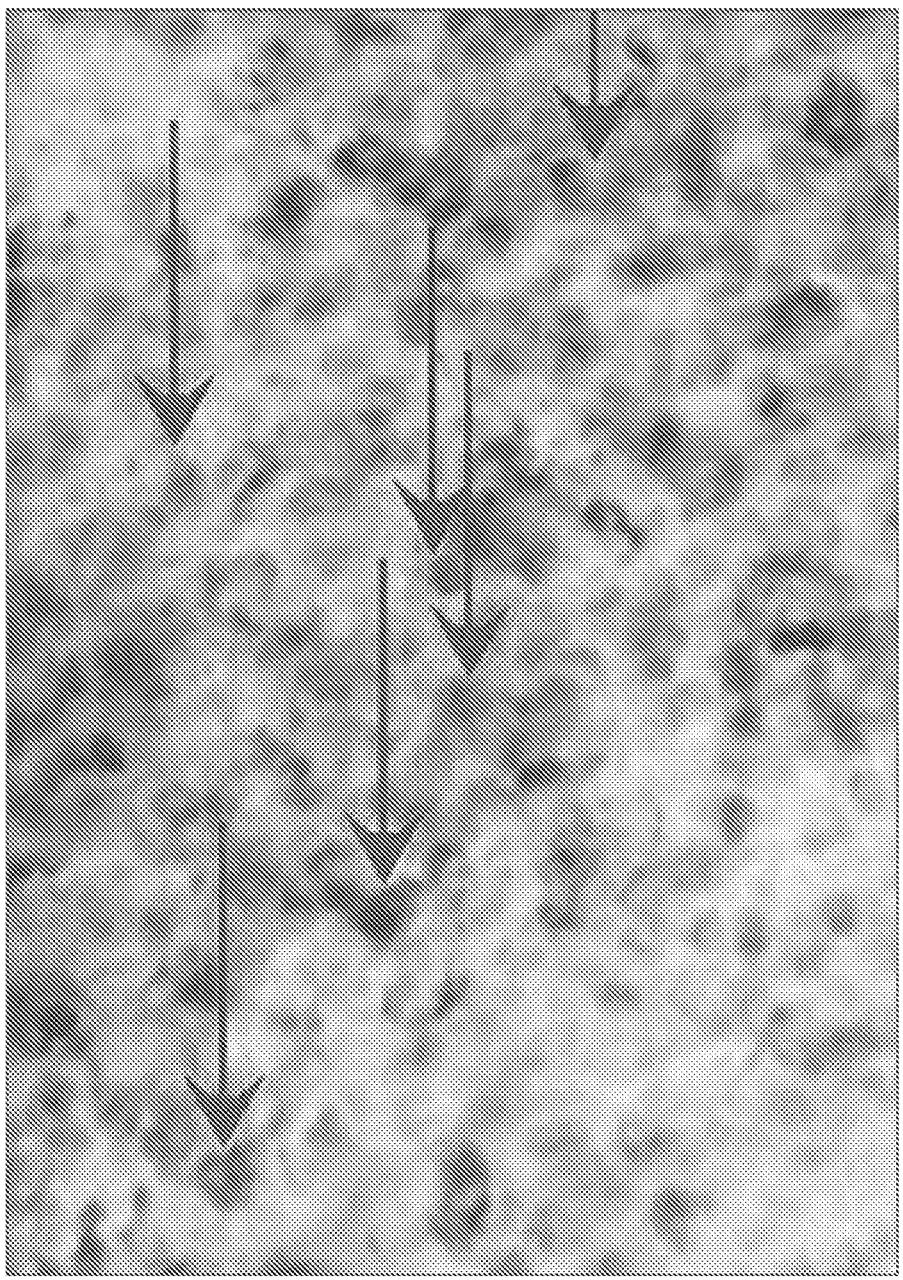
Figures 1, 4B:
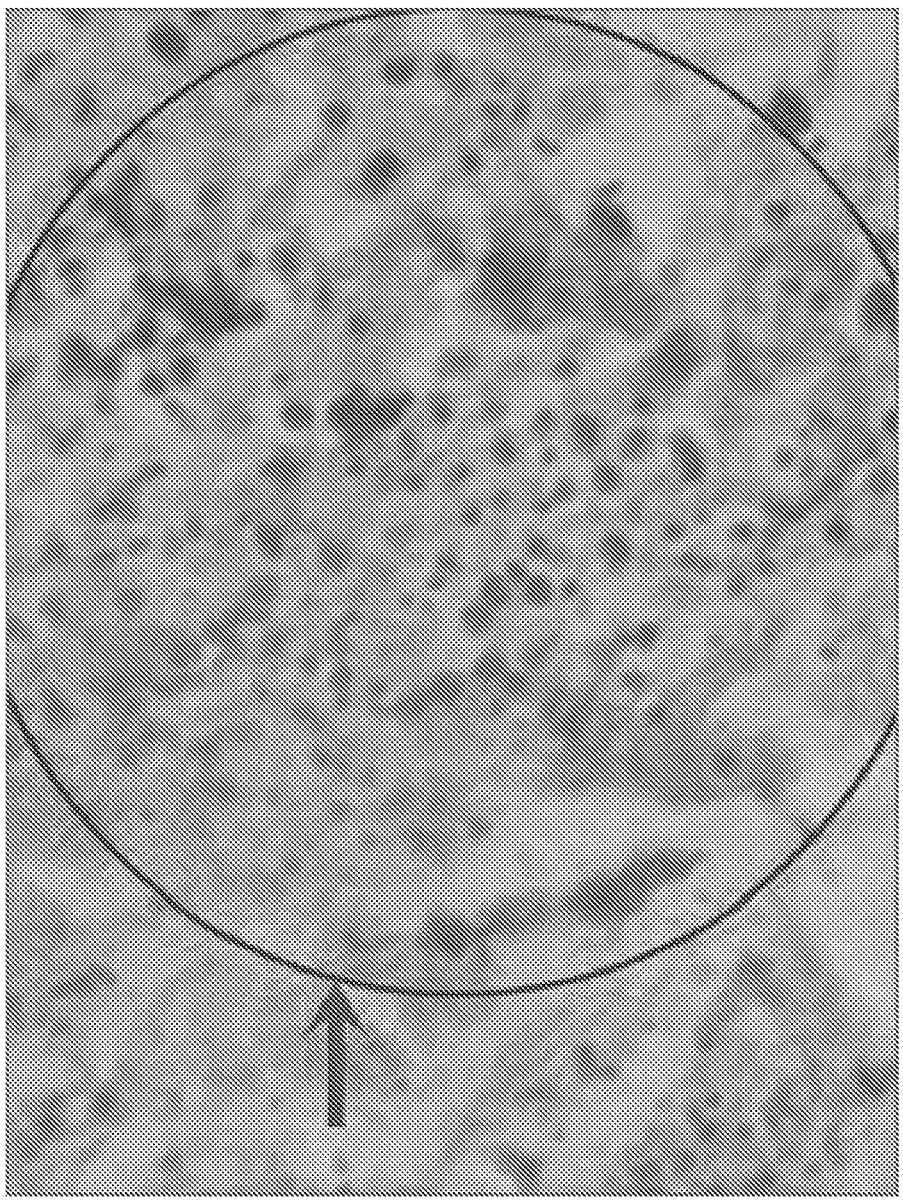
Figures 2, 4B:
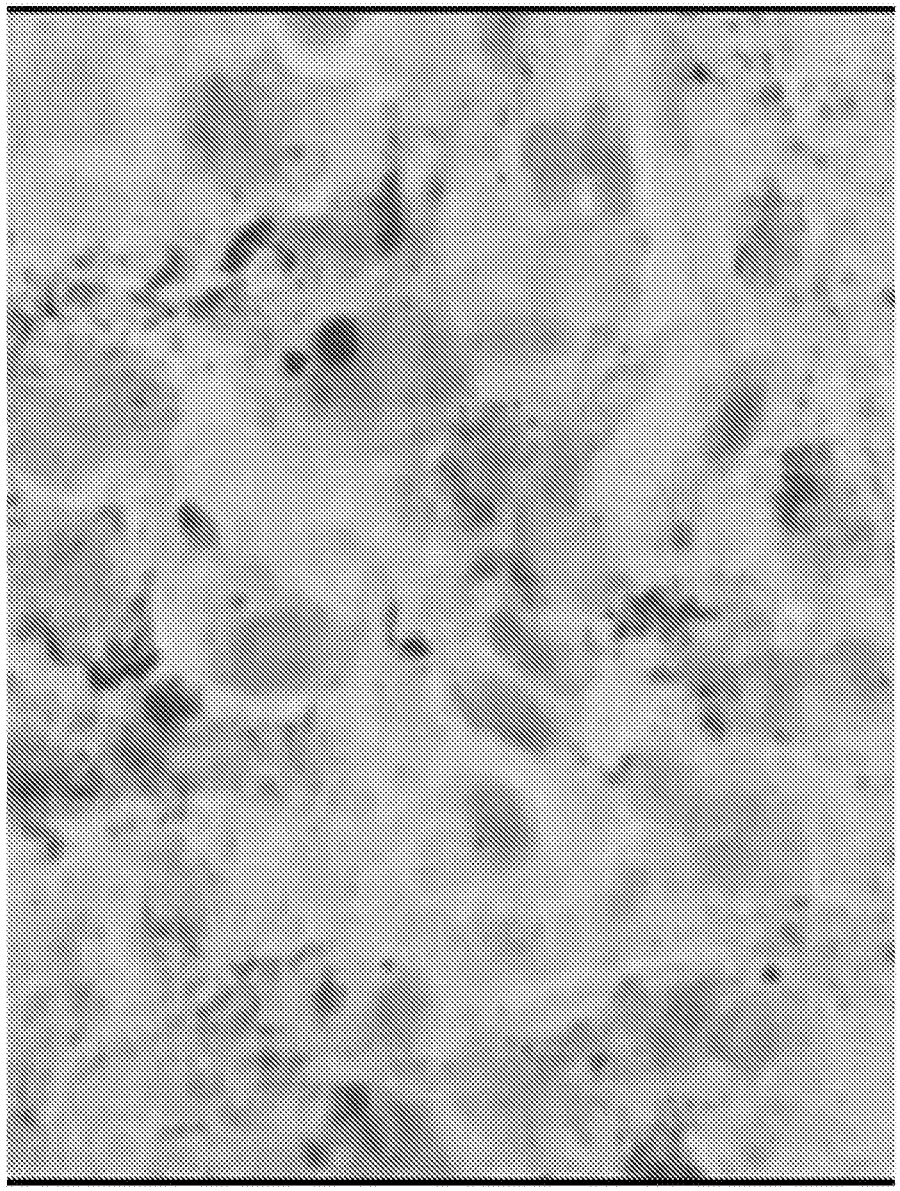
Figures 3, 4A:
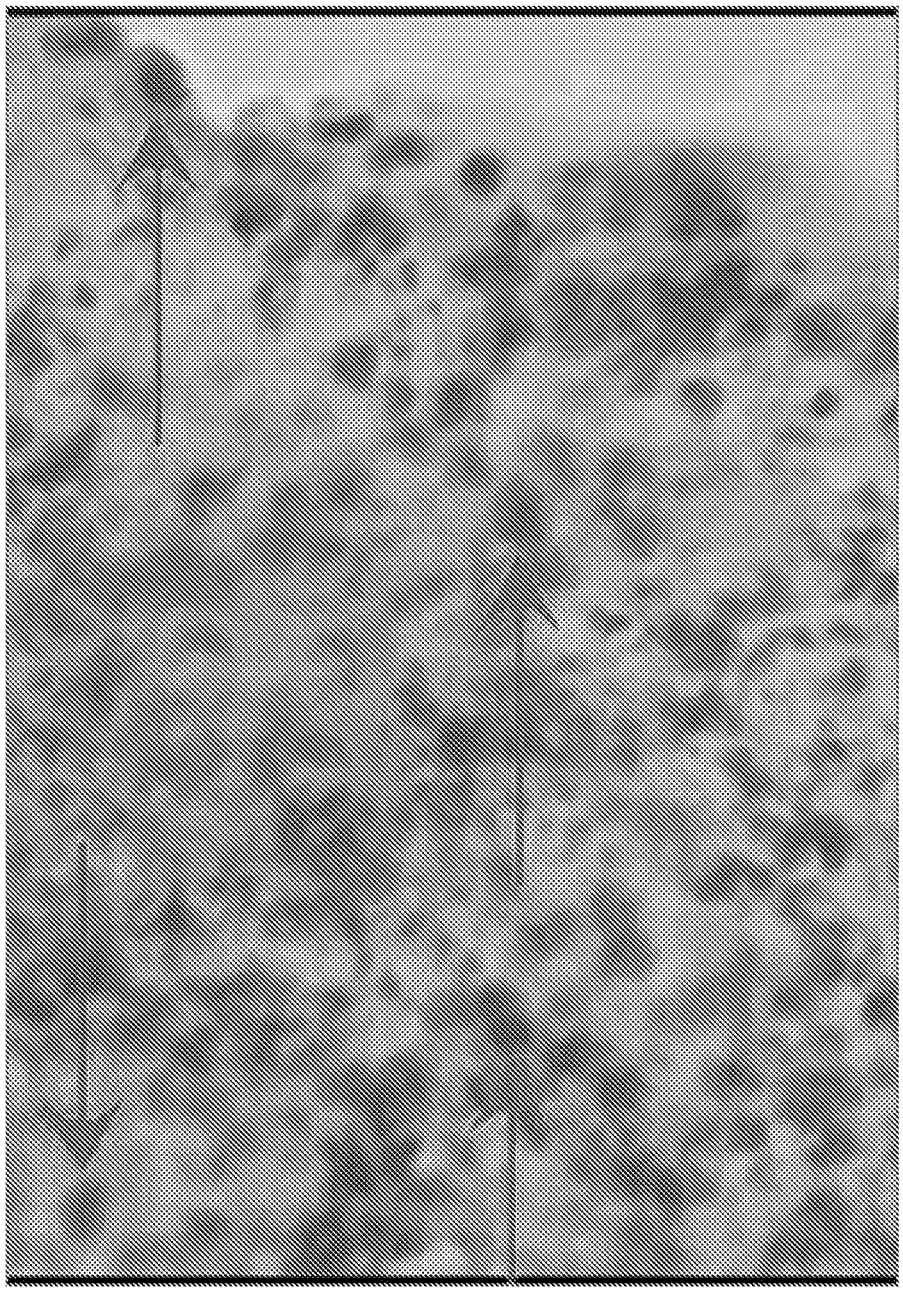
Figures 3, 4B:

Overall Survival (OS) (censored observations, surviving patients in follow-up ranged from 6-36 months), with 6.45 months median survival time in UMIPIC-therapy compared to 4.98 months median survival time in ITCT, showed a significant difference (p<0.05, Table.4). Curves (Kaplan-Meier) for both groups are depicted in FIG. 3. Table 4 shows that the median survival time and 6-month survival rate in UMIPIC and ITCT groups were 6.45 months vs 4.98 months and 64% vs 45%, respectively (P<0.05). One-year survival rate in UMIPIC was 28% with a remarkable improvement compared to 5% in ITCT (P<0.05).

TABLE 4

Comparison of the survival time between the UMIPIC and ITCT groups

| Groups | n | Mean survival/ month | Median survival/ month | log-rank Chi square | P | 6-month survival rate/% | Chi square | p | 1-year survival rate/% | Chi square | p |
|---|---|---|---|---|---|---|---|---|---|---|---|
| UMIPIC | 25 | 6.95 | 6.45 | 5.586 | 0.018 | 64 | 1.62 | >0.05 | 28 | 4.02 | 0.045 |
| ITCT | 20 | 5.37 | 4.98 | | | 45 | | | 5 | | |

The patients had temporary mild fever (not over 38° C.) for a few hours and minor injection pain after the intratumoral injection of UMIPAC-therapy solution, but with no severe complications. No other significant systematic or local adverse effects were observed. No bleeding in the needle track or side effects such as myelosuppression, neutropenia, thrombocytopenia, GI toxicity, or apparent loss of hair/loss of appetite were noted.

Pancreatic cancer is an aggressive carcinoma characterized by marked invasiveness and a propensity for distant metastases. Although only less than 20% of patients with pancreatic carcinoma are surgically resectable, surgery-associated complications are very common. Pancreatic carcinoma is also associated with high tissue concentrations of multidrug-resistant genes, therefore advanced pancreatic cancers can be resistant to conventional treatment protocols, leading to suboptimal therapeutic outcome (Muchmore, et al., Proc 3rd Intl Cong Neo-Adjumvant Chemotherapy (1991) 236-238; Taniguchi et al., Cancer (1989) 64:2001-2006). Therefore, in order to minimize toxicities and maximize therapeutic efficacy, alternative drug-delivery routes may be vital to achieve such clinically therapeutic goals. Of all the drug-delivery routes, the percutaneous intratumoral approach combined with hapten-enhanced chemoimmunotherapy in our studies has been regarded as a new research direction of choice, with the greatest potential for prolonging survival time and enhancing the quality of life in unresectable pancreatic cancer patients (Lygidakis et al., Ann Surg (2002) 236(6):806-13). This is achieved by increasing drug concentration levels at the tumor sites higher than chemoembolization, while minimizing systematic drug exposure and toxicity to the whole body (Collins J M, J Clin Oncol (1984) 2:498-504).

First:

Immediately after the intratumoral injection the oxidant can effectively coagulate the tumor mass by disturbing the blood vessel in the tumor, which ultimately leads to a higher concentration of the injected drug within the coagulated tumor mass. This improves the drug utilization by extending the duration of drug action and reducing its dosing frequency. The coagulation mentioned above refers to a process that transforms the neoplastic tumor mass to a soft or semisolid mass. This transformation results in suppression of tumor metabolism which could ultimately also lead to higher expression of fibrosis (FIG. 3), and destroy the environmental condition for tumor cell growth. This transformation is shown in earlier animal studies and clinical research (Qiong et al., J Shandong Univ (2007) 45:988-992). In many cases more than 90% of the neoplastic cells were killed in a UMIPIC solution-reached tumor. In general, the coagulation process acts like a chemical debulking or surgery that reduces the neoplastic mass burden, while sparing the small living part of the tumor to be treated by subsequent immunotherapy. In addition, coagulation also results in structural changes in the cell surface and extracellular matrix. This ultimately leads to cell lysis with release of cellular contents including tumor antigens in the neoplastic cells, which leads to local inflammatory response. This inflammatory effect, coupled with the presence of added hapten modified with tumor-associated antigens such as mesothelines released from the neoplastic cell lysis by coagulation and chemotherapy, leads to a more complex immunological genesis.

Second:

The chemotherapy drug Ara-C could kill the remaining part of the tumor (after coagulation destroys most of the tumor cells) by blocking the living cancer cell differentiation and proliferation. The effect caused by some cytotoxic drugs induces the production of an immunogenic apoptosis, i.e. the non-immunogenic cell transforms into immunogenic ones in the process of cell apoptosis. For instance, both gemcitabine and doxorubicin could induce immunogenic cells (Nowak et al., J Immunol (2003) 170(10):4905-4913), which may contribute to the various molecular components released from the dead cells as a result of the chemotherapy drug (Casares et al., *J Exp Med* (2005) 202(12):1691-1701). The use of Ara-C in this study is only reported to have an enhancing function for B7 molecules, expressing and activating T cells efficiently to Jurkat cells (a kind of leukemia), but not for cancer cell immunological death (Ming et al., *J Biochem Pharmaceutic* (2009) 30:6-13). Therefore, the role of hapten is important in enhancing the immunological response of tumor-associated antigens.

In addition, the $CD4^+CD25^+FoxP^{3+}$ regulatory T cells are some of the most important immunosuppressive factors. They are greatly inhibited by the cytotoxic drug, leading to enhanced anti-tumor immunity. Chemotherapy can up-regulate CD95 expressed in Treg cells, which further induces apoptosis (compared to the effect of T cells). This indicates that Treg cells may take part in the anti-tumor immune response as a new target (Zhang et al., *Clin Immunol* (2008) 129(2):219-229). Instant coagulation in tumors could kill the Treg cells in a tumor mass following UMIPIC-Therapy, and enhance up-regulation of T cells.

Third:

More than 90% of tumor cells were killed at the site of injection by the coagulated tumor and cytotoxic drug. Thereafter, multiple autologous tumor-associated antigens are released from those dead tumor cells, which trigger a mild immune response as self-vaccination. That is to say the quantity of the autologous tumor-associated antigens is just enough to reach the threshold required for stimulating immune response. Nevertheless, this heightened immunogenicity of the antigens is indispensable to the immune response. Consequently, in the presence of the small molecule hapten inlaying the denatured tumor, the lysed tumor cells in the resulting depot are modified by hapten and generate multiple modified tumor-associated antigens. The released MHC-associated peptides, with more complex immunogenesis, also function as an autologous tumor vaccine. Such a tumor vaccine enhances the patient's own tumor immunogenicity. This stimulates the T lymphocytes against living tumor cells in and around the original tumor (which is unaffected by UMIPIC), with the initial coagulation (along with the metastasized tumor and micro lesions) after the intratumoral coagulation therapy. Our clinical data and animal studies have shown that the immune response significantly improves after UMIPIC-therapy, especially the $CD4^+$ T cell immunity[12]. This autologous tumor vaccination plays an important role in prevention of tumor metastasis and recovery from the original tumor cells. Systematic immunity against patient-specific tumor-associated antigens was boosted by significantly increased and activated APC (including DC and macrophage), which are further recognized by T cells and NK cells, ultimately aiding in suppression and eradication of tumor recurrence and metastatic foci. Also acute inflammation was redefined as a critical component of tumor progression. Inflammatory tumor cells attract different lymphocytes including APC, macrophages and DC, and the activated B cells (which react with tumor-associated antigens such as mesothelines tumor complex antigen, DNA, RNA and other cell lysates (Yu B (2004) [U.S. Pat. No. 6,811,788]; Le et al., *J Immunother* (2013) 36(7):382-9). The lymphocytes exposed to these tumor-associated antigens, especially the antigens modified with hapten (generated from the tumor cell lysis) elicit a tumor-specific immune response. This can encompass hormonal, cellular and complement-mediated responses which further act against the presence of adjacent live neoplastic cells not initially killed by the coagulation effect. Other inflammatory mediators such as TNF and IFN-γ are also involved in anti-tumor growth. Yue-Mei et al. constructed a new mouse tumor model, incorporating a manufactured surgical wound representative of acute inflammation. They found the inhibitory effects of tumor cells in the early phase to be related to IFN-γ secretions in the wound (Ma et al., *J Exper Clin Cancer Res* (2009) 28:2). Consequently, as the "invisible scalpel", tumor-specific immune response is enhanced and affected on the vegetative tumor cells, blocking recurrence and metastasis.

In summary, coagulation (like de-bulking) eliminates at least some (more than 90%) of the neoplastic cells in the tumor targeted with anti-neoplastic agents, which kill the left-over live neoplastic cells not initially killed by UMIPIC. The in situ "vaccination" further eliminates live neoplastic cells, which results in better therapeutic efficacy than other therapeutic options. Therefore it is reasonable to conclude that UMIPIC is a relatively safer and more efficacious option, especially for patients with advanced stage disease. More effective controls of the disease is strongly needed.

Example 2

Hapten-Enhanced Therapeutic Effect in Advanced Stages of Lung Cancer by UMIPIC Therapy UMIPIC is a new option for cancer treatment, as it integrates local chemotherapeutic effect with systematic antitumor immunity by intratumoral drug delivery. We have applied UMIPIC in the treatment of advanced lung cancer with a compounded solution including three components, i.e. an oxidant, a cytotoxic drug (Cytosine Arabinoside: Ara-C) and hapten. Previous animal studies showed that clinically approved oxidant can effectively coagulate tumor mass thoroughly by denaturation, which kills more than 90% of tumor mass, reduces blood flow and entraps the injected cytotoxic drugs at a high concentration within the coagulated tumors (>10× than conventional chemotherapy) for sustaining drug release (Baofa Yu (2004) [U.S. Pat. No. 6,811,788 B2]). The cytotoxic drug Ara-C can continues to kill tumor cells that were not destroyed by coagulation, at the same time, autologous tumor associated antigens were also released from the dead tumor to trigger immune response as a self-vaccination. Meanwhile, hapten binds to the tumor associated antigens to increase the specificity of these antigens and further boost systematic hormonal and cellular immunity for suppression and eradication of tumor recurrence and metastasis. In the last decade, we have tried this treatment using combination of drugs with or without hapten in patients with advanced lung cancer. The data from the two groups were collected and analyzed, and the role of hapten (Baofa Yu (2004) [U.S. Pat. No. 6,811,788 B2]) in UMIPIC was evaluated.

Materials and Methods

Patient Selection and Data Collection

Ninety-seven of the 120 patients in advanced stages of lung cancer were enrolled in the study, and the complete survival data obtained were analyzed. Test group patients (n=55) received UMIPIC, in which 19/55 of the patients received two cycles of treatment with UMIPIC, and 20/55 of the patients received UMIPIC without adjuvant treatments. Control group patients (n=42) received ITCT, in which 29/42 of the patients received two cycles of treatment with ITCT, and 13/42 of the patients received ITCT without adjuvant treatments. Patients were informed of the study details and agreed to participate by signing written informed consent. Hospital ethical committee also approved this study. Confirmed by imaging and pathologic examination or cytological diagnosis, primary lung cancer patients in advanced stages and/or with metastatic cancers from November 1999 to September 2006 were analyzed. Data was collected from case report forms (CRFs) filed by physicians from their hospitals. There were three available contents; clinical characteristics data, follow-up time and response data (Table 1). For each patient, the first follow-up visit was scheduled one month after treatment initiation and then scheduled on a monthly basis. The records were updated after each follow-up visit.

ITCT and UMIPIC Preparation

The solution of drugs for UMIPIC was freshly prepared before each intratumoral injection with clinically approved components including an oxidant, a cytotoxic drug and hapten; and the solution for ITCT contains an oxidant and a cytotoxic drug, but without hapten.

Treatment Delivery

All patients had a lung CT scan as a pretreatment baseline. Routine examination of cardiopulmonary function was also done. Bucinnazine hydrochloride injection (0.1 g) and hemocoagulase atrox for injection (1 KU) were injected intramuscularly with the patient lying supine or laterally for accurate location. Prior to UMIPIC, the patients were asked to fast without water for 14 hours prior to this therapy in order to avoid side effects and infections from this therapy. After routine disinfection, draping and local anesthesia with 2% lidocaine, the 25 Gauge spinal needle was inserted into the tumor under CT guiding, and needle tip in tumor was monitored by CT, the core of the needle was taken out and the inflator was connected and used as a high pressure syringe (inflation device, 30 atm/bar, Merit Medical, Utah, USA), then the injection of solution was performed.

UMIPIC and ITCT have a same therapeutic procedure, which are minimally invasive and simple like a needle biopsy. UMIPIC or ITCT was delivered by a spinal needle inserted into the tumor, and the solution was pressurized (at the level of atmospheric pressure) to obtain full distribution of clinically approved regimens in the tumor under CT imaging guidance. Picker IQ CT was used for single slice scanning and monitoring the density changes of CT value at a point or area of interest in the lung tumor. Special attention was needed for monitoring the density changes of CT value at margins of tumor surrounding to ensure full distribution of drugs to the margins. Since the drugs in the solution are water soluble, it is better than oil-drug emulsion which is sticky and hard to distribute in tumors. Under high pressure, the combination of drugs in UMIPIC or ITCT could penetrate to full matrix of tumor, even into tumor cells with sustained drug release for a long time. The average time of whole procedure is about 30-45 minutes. Patients with severe cough during the treatment were unable to operate and were excluded from data analysis. The volume of the injection was calculated by the diameter of tumor ($D^r$) times 2 for 1 cm to 5 cm of tumors and $D^r$ times 1.5 for not smaller than 6 cm of tumor; Good Practice is the key for a successful treatment in all cases according to this calculation in order to deliver enough dosage into tumors [FIG. 1]. Having injected with the combined solution, the physicians would observe density values by CT at a point or area of interest of tumor (indicating drug diffusion in the tumor) and related complications such as hemorrhage around the needle track by CT scan imaging. Second and third cycle of treatment was usually required for better efficacies compared to one cycle of treatment. The patients should be re-examined by CT 4 to 6 weeks after the last therapy, and some patients were treated with a second cycle of treatments.

Assessment

The response to treatment was evaluated by solid tumor effect evaluation criterion of EROTC (European Organization for Research and Treatment of Cancer) and RECIST (Response Evaluation Criteria in Solid Tumors) made by NCI (US and Canada) in October 1998 (Duffaud et al., *Bull Cancer* (2000) 87(12):881-886). All case report forms (CRF) were filled by treating physicians of study hospitals.

Statistical Analysis

The statistical analysis was done by Binzhou Medical College. The primary objective was to evaluate the overall survival (OS), which was defined as the duration from the first treatment to patient death and was estimated using Kaplan-Meier analysis. Secondary objective was response rate at 4-6 weeks, defined as the proportion of patients with complete response (CR), partial response (PR), or stable disease (SD) after the treatment, using the RECIST (version 1.0). Comparison of effective rate was calculated with the Chi-square test. Statistical analysis was conducted with SPSS 17.0 statistical software (SPSS Inc., Chicago, Ill., USA); P value of <0.05 was considered of statistical significant.

Results

Patient characteristics: At the end of follow-up, 97 of the 120 patient enrolled complete the study and the survival data of which were analyzed, including 55 patients received UMIPIC and 42 patients received ITCT. In the UMIPIC group, 43 cases were male and 12 were female, aged between 28-76 years old and with a median age of 59±11; 83.6% were diagnosed as in stage m and IV according to tumor-node metastasis (TNM) classification. Histopathology results indicated that 26 (47.3%) of the patients had squamouscell carcinoma, 15 (27.2%) had adenocarcinoma cell carcinoma, and 14 (25.5%) had mixed or uncharacterized lung cancer (Based on biopsy diagnosis). In the ITCT group, 33 cases were male and 9 were female, aged between 19-85 years old and with a median age of 55±12, including 6 (14.3%) patients with adenocarcinoma, 17 (40.5%) with squamous carcinoma and 18 (42.8%) with mixed or uncharacterized lung cancer (Based on biopsy diagnosis). The baseline characteristics of the patients were well balanced between the two groups [Table 5].

TABLE 5

Patient baseline characteristics

| | | UMIPIC | | ITCT | |
|---|---|---|---|---|---|
| | | | % | | % |
| Enrolled patients | | 5 | 56.7% | 2 | 43.3% |
| Se | Male | 3 | 78.1% | 3 | 78.5% |
| | Female | 2 | 21.8% | | 21.4% |
| Median age | | | 59 | | 55 |
| Age range | | | 28-76 | | 19-85 |
| Histology | Squamous carcinoma | 6 | 47.3% | 17 | 40.5% |
| | Adenocarcinoma | 5 | 27.2% | 6 | 14.3% |
| | Large cell carcinoma | | 0 | 1 | 2.4% |
| | Cytological diagnosed cancer | 4 | 25.5% | 18 | 42.8% |
| Stage | Stage I | | 5.5% | 1 | 2.4% |
| Of | Stage II | | 10.9% | 5 | 11.9% |
| disease | Stage III | 0 | 54.5% | 24 | 57.1% |
| | Stage IV | 6 | 29.1% | 12 | 28.6% |
| Tumor | <2 cm | | 7.3% | 3 | 7.0% |
| size | 2-5 cm | 0 | 36.3% | 13 | 30.1% |
| | >5 cm | 1 | 56.4% | 26 | 61.9% |

TABLE 5-continued

Patient baseline characteristics

|  |  | UMIPIC | % | ITCT | % |
|---|---|---|---|---|---|
| Adjuvant treatment | Chemotherapy | 1 | 20.0% | 11 | 26.2% |
|  | Radiotherapy | 8 | 32.7% | 16 | 38.1% |
|  | Prior surgery |  | 1.8% | 1 | 2.4% |
| None of any adjuvant treatment |  | 5 | 45.5% | 14 | 33.3% |
| Disease status | Locally advanced | 5 | 63.6% | 20 | 47.6% |
|  | Metastatic disease | 0 | 36.4% | 22 | 52.4% |

Efficacy Evaluation:

the median OS (censored observations, surviving patients still in follow-up) was 11.23 months in the UMIPIC group and 5.62 months in the ITCT group, respectively [Table 6]. It represents a significant difference between the two groups (5.61 months longer) (P<0.01), with curves (Kaplan-Meier) for all two groups depicted in FIG. 2-1. With a statistical significant difference, the 6-month survival rate was 76.36% (UMIPIC) vs. 45.23% (ITCT) (P<0.01) and 1-year survival rate of 45.45% (UMIPIC) vs. 23.81% (ITCT) (P<0.05) [Table 7]. Notably, the UMIPIC with two cycles of treatment had a survival advantage over the ITCT with two cycles of treatment. We evaluated the efficacy for the patients with two cycles of treatment in UMIPIC and ITCT refined groups, and it showed that 6-month survival rate were 100% vs. 72.41% (P<0.05), and 1-year survival rates were 73.68% (UMIPIC) vs. 37.93% (ITCT) (P<0.05) [Tables 8 & 9]. The median OS was 14 months for UMIPIC and 7 months for ITCT, representing a significant difference (7 months longer) between UMIPIC and ITCT patients with two cycles of treatments (P<0.01), with curves (Kaplan-Meier) for all groups as depicted in FIG. 2-2. Two cycles of treatment demonstrated more powerful debulking in main tumor mass than single cycle of treatment, and providing a better balance point for immunological power to eradicate less load of tumor cells (which is unaffected by UMIPIC) after UMIPIC killing the main mass of tumor.

TABLE 6

Comparison of mean and median survival time between UMIPIC and ITCT groups

| GROUP | N | Mean/month survival | median/month survival | P |
|---|---|---|---|---|
| UMIPIC | 55 | 12.66 | 11.23 | 0.0023 |
| ITCT | 42 | 7.59 | 5.62 |  |

TABLE 7

Comparison of 6-months and 1-year survival time between UMIPIC and ITCT groups

|  |  | 6-month survival rate/% |  |  | 1-year survival rate/% |  |  |
|---|---|---|---|---|---|---|---|
| GTOUP | N | (%) | $\chi^2$ | P | (%) | $\chi^2$ | P |
| UMIPIC | 55 | 76.36 | 9.885 | 0.0016 | 45.45 | 4.838 | 0.028 |
| ITCT | 42 | 45.23 |  |  | 23.81 |  |  |

TABLE 8

Comparison of mean and median survival time with two cycles of Therapies between UMIPIC and ITCT groups

|  |  | Mean survival | median survival | T Test |  |
|---|---|---|---|---|---|
| Group | N | (month) | (month) | T | P |
| UMIPIC | 19 | 16.79 | 14 | 2.806 | 0.007 |
| ITCT | 29 | 10.66 | 7 |  |  |

TABLE 9

Comparison of 6-months and 1-year survival time with two cycles of therapies between UMIPIC and ITCT groups

|  |  | 6-month survival rate |  |  | 1-year survival rate |  |  |
|---|---|---|---|---|---|---|---|
| Group | N | (%) | $\chi^2$ | P | (%) | $\chi^2$ | P |
| UMIPIC | 19 | 100 | 6.290 | 0.012 | 73.68 | 5.880 | 0.015 |
| ITCT | 29 | 72.41 |  |  | 37.93 |  |  |

Figure 5:
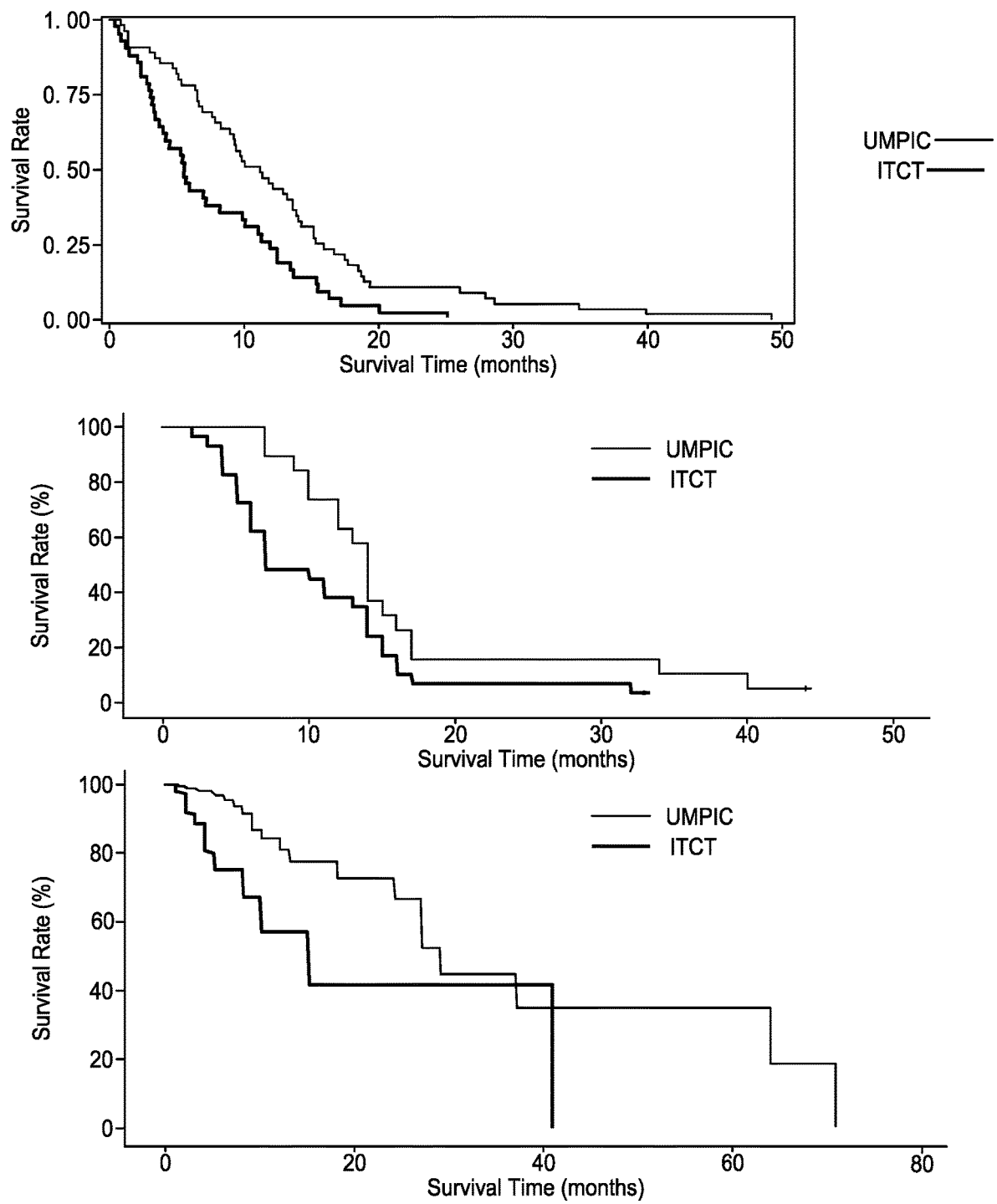
FIG. 5 shows survival curve of UMIPIC.

In the two groups, the complete survival data of 33 patients receiving UMIPIC (N=20) or ITCT (N=13) without adjuvant therapy (surgery, radiotherapy or chemo-radiotherapy) was also analyzed, and it showed a statistical difference in median OS of 11 months vs 4 months (7 months longer) between UMIPIC and ITCT, respectively, without adjuvant treatment (P<0.05) in Table 10. The 6-month survival rate was 80% with UMIPIC vs 30.1% with ITCT (P<0.05), and 1-year survival rate of 50% with UMIPIC vs 15.38% with ITCT (P<0.05, Table 11 and curves depicted in FIG. 5-3). Comparisons of UMIPIC with ITCT [Tables 10 & 11] suggest UMIPIC monotherapy has a better impact on patient survival rate.

TABLE 10

Comparison of mean and median survival time without adjuvant treatments between UMIPIC and ITCT groups.

| GROUP | N | Mean (month) | survival | Median survival (month) | T | P |
|---|---|---|---|---|---|---|
| UMIPIC | 20 | 19.1 |  | 11 | 2.177 | 0.037 |
| ITCT | 13 | 7.54 |  | 4 |  |  |

TABLE 11

Comparison of 6-month and 1-year survival time without adjuvant treatments between UMIPIC and ITCT groups.

|  |  | 6-month survival rate/% |  |  | 1-year survival rate/% |  |  |
|---|---|---|---|---|---|---|---|
| GROUP | N | (%) | $\chi^2$ | P | (%) | $\chi^2$ | P |
| UMIPIC | 20 | 80 | 4.51 | 0.004 | 50 | 4.08 | 0.043 |
| ITCT | 13 | 30.1 |  |  | 15.38 |  |  |

The response rates (CR+PR+SD/TOTAL) were 81.8% and 83.3% in UMIPIC and ITCT groups, respectively, indicating no significant difference (P=0.055) [Table 12]. It is necessary to note that the slight size increase of the tumor mass was observed clinically in both groups at first CT examination, which was likely due to inflammatory response induced by coagulation, while after addition of haptenin UMIPIC, more activities of immunological response with inflammations were induced (Goldberg et al., Proc Nano Science and Technology Inst (*NSI*) (2006) 2:1-4; Hogenesch H., *Vaccine* (2002) 20(3):34-39). Encouragingly, some of the remarkable responses in advanced cancer patients provided proof of the greatest effect on patients in UMIPIC [FIG. 6-1, FIG. 6-2].

TABLE 12

Therapeutic response between UMIPIC and ITCT groups

| Effect | UMIPIC N | % | ITCT N | % | TOTAL N | % | P |
|---|---|---|---|---|---|---|---|
| CR | 2 | 3.6 | 3 | 7.1 | 5 | 5.2 | 0.055 |
| PR | 5 | 9.1 | 12 | 28.8 | 17 | 17.5 | |
| SD | 38 | 69.1 | 20 | 47.6 | 58 | 59.8 | |
| PD | 10 | 18.2 | 7 | 16.7 | 17 | 17.5 | |
| TOTAL | 55 | 100.00 | 42 | 100.00 | 97 | 100.00 | |
| CR + PR (%) | | 12.7 | | 35.9 | | 22.7 | |
| CR + PR + SD (%) | | 81.8 | | 83.3 | | 82.5 | |

Complication: the related complications include temporary mild fever (not over 38° C.) for a few hours, minor pain at injection area, aerothorax in 4 cases and leukocytopenia (within normal range) [Table 13]. There were no patients with hemorrhage around the tumor and observed needle track after therapy. No significant systematic or local adverse effects were observed, and side effects such as myeloid suppression, neutropenia, thrombocytopenia, GI toxicity, apparent loss of hair or appetite were not observed.

TABLE 13

Related complications of UMIPIC and ITCT groups

| Complication | UMIPIC N (%) | ITCT N (%) | P |
|---|---|---|---|
| Minimal Local pain | 3 (5.5) | 7 (16.7) | 0.07 |
| Aerothorax | 2 (3.6) | 2 (4.7) | 0.78 |
| Leukocytopenia | 15 (27.2) | 8 (19.0) | 0.34 |
| Mild fever | 16 (29.1) | 7 (16.7) | 0.15 |
| Slight cough | 6 (10.9) | 7 (16.7) | 0.41 |
| Nausea | 1 (1.8) | 2 (4.7) | 0.40 |

Worldwide, lung cancer is still one of the major deadly diseases. Local treatment like surgery and radiotherapy are the primary curative therapies for patients in early stages of lung cancer. About 54% of patients present a metastasis at diagnosis due to lack of clinical symptoms at early stages, which tend to result in an extremely poor prognosis with an overall 5-year survival rate of 3.8% (Wright et al., *Thorax* (2006) 61:597-603). For most advanced lung cancers, standard chemotherapy generally is the mainstream of management involving Pemetrexed (Zimmermann et al., *Lancet Oncol* (2012) 13:247-255; Baldwin et al., *Drugs* (2009) 69:2279-2302), Oxaliplatin (Cappuzzo et al., *British Journal of Cancer* (2005) 93:29-34) and Docetaxel (Komiyama et al., *British Journal of Cancer* (2012) 107:1474-1480), but apparently it has reached a plateau with disappointing outcomes (Schiller et al., *N Engl J Med* (2002) 346:92-98). Despite the introduction of a series of targeted drugs for patients with epidermal growth factor receptor (EGFR) mutations (Gefitinib or Erlotinib) (Mok et al., *N Engl J Med* (2009) 361:947-957; Maemondo et al., *N Engl J Med* (2010) 362:2380-2388) and ALK rearrangement (Crizotinib) (Takaaki et al., *Clin Cancer Res* (2011) 11(23):7213-7218) in the past decade, the survival rate still has not been significantly improved. Today, immunotherapeutic interventions including vaccine therapy derived from lung cancer cell lines (or tumor associated antigens) and immune-stimulatory checkpoint antibodies, may improve outcomes in lung cancer, although traditionally not considered to be a possible treatment for tumor. Moreover, the combination of immunotherapy and chemotherapy or chemoimmunotherapy has been successfully applied clinically (Reck et al., *J Clin Oncol* (2013) 31:abstr LBA8011; Sandler et al. *N Engl J Med* (2006) 355:2542-2550; Reck et al. *Ann Oncol* (2010) 21:1804-1809).

UMIPIC in this clinical study is a patented therapeutic method for solid tumor, and was explored in this clinic with personalized dosage based on tumor-size while utilizing patient-specific in vivo modified autologous tumor antigens of patient as a self-vaccination to tumor-specific response. The regimen is a personalized and freshly prepared compound solution containing an oxidant, a cytotoxic drug and hapten. Each component plays a vital role in the therapy.

Figure 7:
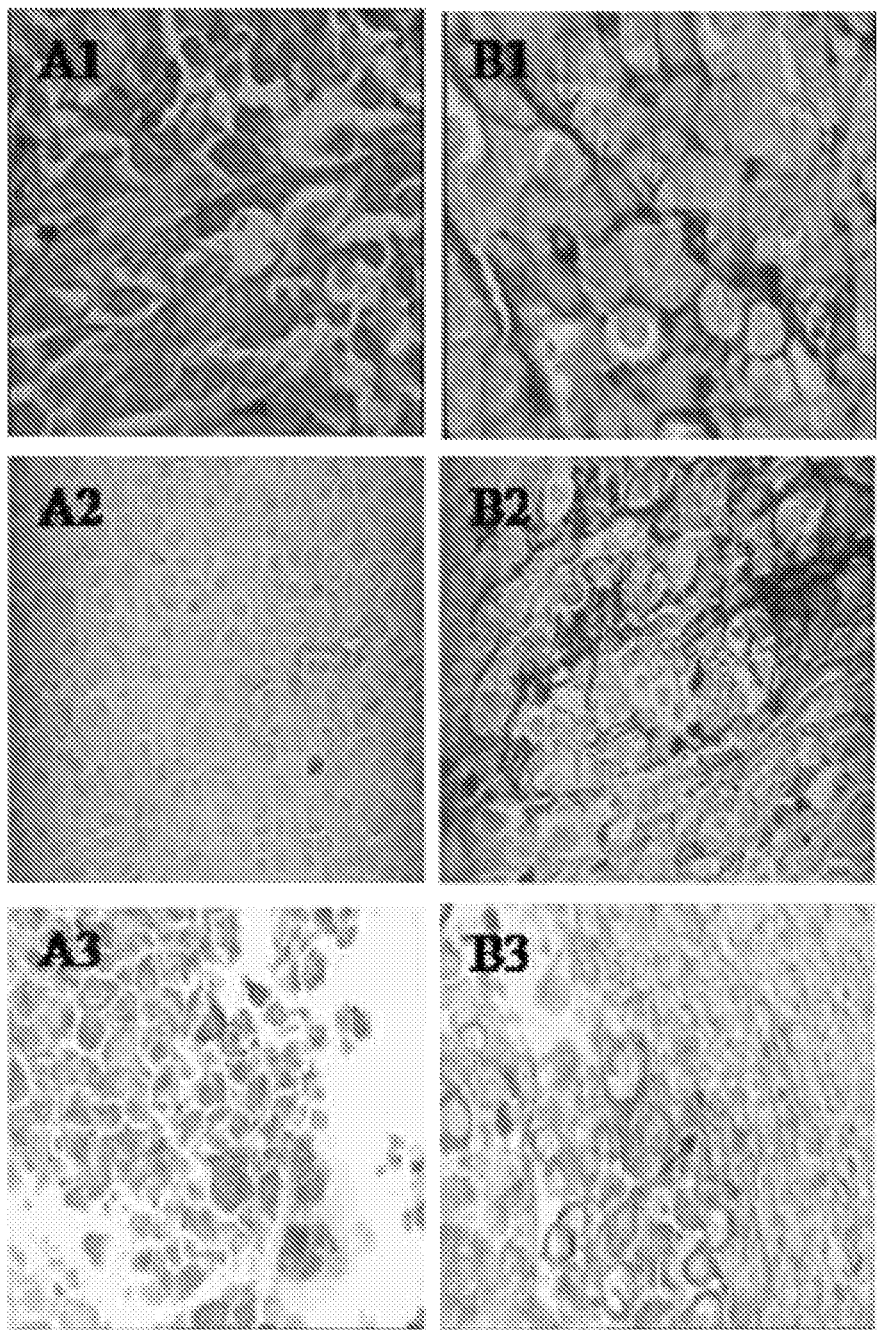
FIG. 7 shows expression of fibrosis under specific staining (EM). A: In control group of ITCT, after 7 days of treatment, tumor was resected to obtain pathological sections for specific staining including elastic fiber staining (A1), reticular fiber staining (A2) and collagen staining (A3); lower expression of the three fibers in tumor were induced by single cytotoxic drug ARA-C. B: In test group of UMIPIC, after 7 days of treatment, tumor was resected to obtain pathological sections for specific staining including elastic fiber staining (B1), reticular fiber staining (B2) and collagen staining (B3); higher expression of the three fibers in tumor were induced by cytotoxic drug ARA-C with hapten, which could limit the tumor growth or destroy of environmental condition for tumor cell growth. A1 and B1 represented the elastic fiber stain in tumor tissue (×200); A2 and B2 represented the reticular fiber stain in tumor tissue (×200); A3 and B3 represented the collagen fiber stain in tumor tissue (×200).

Intratumoral therapy, characterized as high local drug concentrations with minimal systematic toxicity, is an outstanding and attractive alternative to systematic treatment with increasing evidence of its clinical benefits (Tohda et al., *Chemotherapy* (1999) 45:197-204; Jackson et al., *Cancer Res* (2000) 60:4146-4151). The intratumoral delivery approach, integrated with the coagulation induced by the oxidant, can significantly increase the local accumulation of drugs (up to 10-100× that of systematic administration) (Baofa Yu (2004) [U.S. Pat. No. 6,811,788 B2]; Brincker H., *Crit. Rev. Oncol. Hematol.* (1993)15:91-98). In the process of anti-tumor studies, the oxidant acts as the main force in the debulking of the main tumor through coagulation, while the drug Ara-C continues to kill the residual ones. The coagulation effect can effectively change extracellular matrix (EM) and alter the morphological and biochemical components of the tumor such as collagen, elastic fibers, reticular fibers, fibronectin, proteoglycans, hyaluronic acid and other large molecules, obtaining a soft, semisolid or solid mass, with destroyed metabolism and induced fibrosis generation [FIG. 7]. It may also destroy the environmental condition for tumor cell growth and was proven in our previous animal experiment (Qiong et al., *J Shandong Univ.* (2007) 45(10): 988-992). Therefore, coagulation is one of the major causes of improving drug utilization by extending the duration of drug action, as well as systematic drug exposure through sustained drug release, with greatly reduced toxicity (Collins J M, *J Clin Oncol* (1984) 2:498-504).

Figure 8:
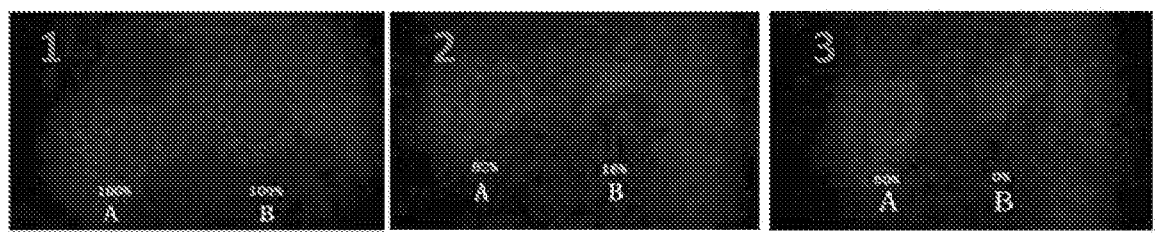
FIG. 8 shows comparison of retention rate of Ara-C with and without intratumoral injection of oxidant Fifteen minutes after injection of Ara-C with cytotoxic oxidant (A group) and Ara-C alone (B group), with the retention rate of 100% in both of A and B groups. Four hours after injection of Ara-C with cytotoxic oxidant (A) and Ara-C alone (B), with retention rates of 80% (A) and 16% (B). Twenty four hours after injection of Ara-C with cytotoxic oxidant (A) and Ara-C alone (B), with the retention rate of 60% (A) and 0% (B). This is a clinical pharmacology study in a hepatocellular carcinoma patient with two tumor masses under nuclear camera; 99 Tcm labeled Ara-C was successful with a 99.9% labelling rate measured; 0.5 mCi of 99 Tcm-Ara-C in cytotoxic oxidant (A) and same dose of 99 Tcm-Ara-C in normal saline (B) were injected into two tumors at the same liver and observed for 99 Tcm of isotopes activities at different time points under SPECT GEStarcom400.

A sustained-release was observed in another clinical study. We separately performed intratumoral injection of 99Tcm labeled Ara-C combined with an oxidant and the 99Tcm-Ara-c alone in two tumor masses in the same liver of a HCC patient. We found the drug retentions are 82% vs. 16% at 12 hours in each tumor, and 60% vs. 0% within the tumor at 24 hours in each tumor after injection, respectively [FIG. 8]. Moreover, in the presence of the inflator, it is particularly important to note the advantage of this approach, including high-sustaining and homogeneous drug diffusion in tumor, could present a satisfying clinical outcome.

Compared with chemotherapy, the side effects of UMIPIC include mild fever, local pain and accidental aerothorax in 4 cases in this study, but all with an improved quality of life. Aerothorax is one of the related complications of biopsy in the chest (Zhenlu et al., *Chin J Interv Imaging Ther* (2013) 10: 275-278). Although it only happened in a few patients and recovered spontaneously afterwards. However, to reduce the possibility of aerothorax, it is suggested to keep the syringe with compounded solution before withdraw the needle, and the patients were asked to inhale to block the needle track. A shortest distance and an ideal angle to puncture into the tumor are the prerequisites to avoid complications. Latent metastatic cells brought along the needle track are killed by drops of compounded solution left in the needle track, so no cases with local metastasis were found in our study.

Creating an in-situ vaccine depot in tumor due to tumor-specific antigen releasing by killed tumor cells is another intriguing factor in the process of intratumoral chemotherapy (Goldberg et al., *J Pharm Phamnnacol* (2002) 54:159-180). Furthermore, UMIPIC can not only induce the in-vivo vaccine-like effect, but also enhance significantly the systematic immunity by addition of hapten. When multiple autologous tumor antigens were released from the apoptotic or necrotic tumor cells induced by the coagulation and cytotoxic drug, cell death can be a priming event for T cell response and can induce potent immunity. These cell deaths were called a "good death" (Nowak et al, *Adv Dnrg Deliv Rev* (2006) 58(8):975-990; Lake et al., *Nat Rev Cancer* (2005) 5(5):397-405), which elicit a weak immune response as an in vivo self-vaccination promoted by immunologic modulator, i.e., small molecule hapten inlaying the denatured tumor; and the modified cell debris or matrixes with tumor antigens became a new complex, more specific to the host immune system. This will generate stronger tumor antigens referred to as an autologous tumor vaccine, making the tumor itself more immunogenic to cancer cells.

In view of the optimistic survival advantage of UIMPIC-Therapy, we further analyzed the UMIPIC group combined with conventional treatments. The median OS of UMIPIC with combination treatments was 11.23 months (Table 6), and the UMIPIC alone was 11 months (Table 10), indicating the combination treatment may not sufficiently prolong the survival time compared with UMIPIC alone. In addition, according to clinical observation, the patients received two cycles of treatment with UMIPIC had a median OS of 14 months (Table 8) and superior survival rate (Table 9) compared to single cycle of treatment. It may attribute to the long term immunological memory induced by constitutive releasing of antigens, leading to more effective antitumor response. With less load of tumor, the debulking effect of UMIPIC resulted in better control of residual cancer cells by immunological cells.

It is presumed that the inflammatory response, induced by coagulation and hapten, may also be involved with the anti-tumor immunity. The migration of APCs to the inflammatory tissue can enhance the capture and processing of tumor associated antigens released from the death tumor to draining lymph nodes by APCs. This drives a desired antigen-specific immune response to further eradicate cancer cells at distant sites (Ribas et al., *J Clin Oncol* (2003) 21:2415-2432).

The systematic immunity against patient-specific tumor associated antigens was significantly boosted by increasing the presentation of antigens modified with hapten via APCs (including DC and macrophage) to class I and class H pathways (to $CD4^+$ and $CD8^+$ T cells), respectively. It has the potential to generate responses of immune effectors and immune-memory (Dredge et al., *Cancer Immunol Immunother* (2002) 51,521-531; Ho et al., *J Biomed Biotechnol* (2011) 2011:250-860), to recognize and destroy the residual lung cancer cells that initial coagulation missed in and around the primary tumor and micro-lesions after the UMIPIC. Examples of the elevation of systematic immune response were observed in our animal trial with high levels of CD4+/CD8+(Qiong et al., *J Shandong Univ.* (2007) 45(10):988-992).

The clinical study showed that UMIPIC can induce a more inflammatory response in local tumors and showed a significantly prolonged survival time for patients with advanced lung cancer compared with ITCT in all aspects (Tables 6-11), and the addition of hapten in UMIPIC demonstrated a significant role as immunological booster in terms of prolonged survival time.

In summary, UMIPIC for lung cancer is a non-invasive and effective therapy with a satisfying profile of high specificity and prolonged survival time. It offers a prospect of tailoring treatments much more precisely and could lead to a better response, especially in patients in advanced stages of inoperable or drug-resistant types of lung cancer.

Example 3

Hapten-Enhanced Therapeutic Effects in Advanced Hepatocellular Carcinoma by Tumoricidal Chemoimmunotherapy (TCIT) and Intratumoral Chemotherapy (ITCT)

TCIT integrates local chemotherapeutic effect with systemic antitumor immunity by intratumoral drug delivery. We have applied TCIT with a combined drug in the treatment of advanced HCC. It contains three components: an oxidant, a cytotoxic drug (cytosine arabinoside: Ara-C) and a hapten. This improves drug utilization by extending the duration of drug action and reduces dose frequency. While the injected drug Ara-C continues to kill tumor cells that were not destroyed by coagulation, autologous tumor-associated antigens released from the dead tumor cells killed by coagulation (or Ara-C) then trigger immune response as a self-vaccination.

Meanwhile, a small molecule (hapten) binds to these antigens (and other large carriers) to further boost systemic hormonal and cellular immunity for suppression and eradication of tumor recurrence and metastasis. The data were collected and analyzed. The primary objective of this retrospective cohort study was to assess the feasibility, safety and efficacy of TCIT versus injection of intratumoral chemotherapy drugs (ITCT). The role of hapten was evaluated.

Materials and Methods

Patient Selection and Data Collection

Patients were informed of the study procedure details and agreed to participate by signing informed consent. Confirmed by imaging and pathologic examination, primary HCC patients with local advanced and/or metastatic cancer were retrospectively analyzed. Some received TCIT and others treated with ITCT alone (without hapten). All patients signed the patient consent information for TCIT and the consents were approved by the hospital ethics committee (98-23). Data was collected from case report forms (CRFs) completed by hospital physicians. Collected data included clinical characteristics, follow-up time and response data. For each patient the first follow-up visit was scheduled two weeks after treatment initiation and then on one-month intervals. Median follow-up time was 6 months. The records were updated during each follow-up visit.

TCIT and ITCT Preparation

The combined drugs were freshly prepared before each injection with a clinically approved regimen of an oxidant, a cytotoxic drug (with/without hapten) for intratumoral delivery. The drugs were injected into the tumor with a spinal needle linked to a dilator as a high pressure syringe (BD Inc., Calif.).

Treatment Delivery

All patients had either a pretreatment ultrasound or CT scan of the liver as a baseline. Routine examination of cardiopulmonary function was also done before the treatment. The laboratory blood tests included hepatitis B and C virus antigen/antibodies, serum alpha-fetoprotein (AFP), serum albumin (Alb), serum total bilirubin (Tbil), and alanine aminotransferase (ALT). Bucinnazine hydrochloride (100 mg) and hemocoagulase atrox for injection (1 KU) were injected intramuscularly. The patients were kept in supine or lateral decubitus positions to accurately locate the injection sites. After routine skin preparation, draping and local anesthesia with 2% lidocaine, under ultrasound or CT guidance, the spinal needle was introduced into the tumor in a certain angle. When the needle reached the necessary depth of tumor, the drugs were delivered through the dilator to the needle at the level of atmospheric pressure to facilitate diffusion of the drug within the tumor (FIG. 1). Having injected with the combined solution of twice the tumor diameter (ml), the physicians observed the intratumoral drug diffusion and related complications such as intratumoral hemorrhage and bleeding around the pin track. The whole procedure took about 30-45 minutes. Patients were closely watched for two hours post-injection for any side effects and were further monitored for 5-7 days to decide whether more injections were needed. Injections were repeated at one or two-week intervals if needed for better efficacies. The patients should be re-examined by CT or ultrasound 4-6 weeks after the last treatment.

Assessment

The response to treatment was evaluated by solid tumor effect evaluation criterion of EROTC (European Organization for Research and Treatment of Cancer) and RECIST (Response Evaluation Criteria in Solid Tumors) made by NCI (National Cancer Institute) (US and Canada) in October 1999 (Duffaud et al., *Bull Cancer* (2000) 87(12):881-886).

Statistical Analysis

Statistical analysis was performed. The primary objective was to evaluate the overall survival (OS), which was defined as the duration from the first hospitalization date to the death date and estimated according to the Kaplan-Meier analysis. Secondary end point time was response rate at 4-6 weeks, defined as the proportion of patients with a complete response (CR), partial response (PR), or stable disease (SD) according to RECIST (version 1.0). Response rates and survival rate were analyzed and statistical differences between groups were based on the Chi-square test. The statistical analysis was conducted with SPSS 17.0 statistical software (SPSS Inc., Chicago, Ill., USA); P value of <0.05 was considered to indicate statistical significance.

Results

Patient characteristics: at the end of follow-up a total of 339 patients (male:female ratio 285:54) with complete survival data were included in this study. 214 patients received TCIT with hapten and 125 patients received ITCT without hapten. Most of them were staged as stage III according to the tumor-node metastasis (TNM) classification with over 5 cm diameter. The baseline characteristics of the patients were well balanced between the two groups (Table 14).

TABLE 14

Patient's baseline of characteristics

| | ITCT | | TCIT | |
|---|---|---|---|---|
| | N | % | N | % |
| Enrolled patients | 125 | 36.9% | 214 | 63.9% |
| Sex | | | | |
| Male | 101 | 80.8% | 184 | 85.9% |
| Female | 24 | 19.2% | 30 | 14.1% |
| Albumin(g/L)mean(SD) | 37.9 | | 37.1 | |
| Total bilirubin (mmol/L)mean(SD) | 61.92(n = 96) | | 44.83 (n = 150) | |
| Liver cirrhosis(%) | 42 | 33.6% | 102 | 47.7% |
| AFP(μg/L) | | | | |
| <20 | 28 | 22.4% | 73 | 34.1% |
| 20-400 | 69 | 55.2% | 111 | 51.8% |
| >400 | 28 | 22.4% | 30 | 14.0% |
| Stage of disease | | | | |
| StageI | 2 | 1.6% | 1 | 0.46% |
| Stage II | 46 | 36.8% | 36 | 16.8% |
| Stage III | 46 | 36.8% | 91 | 42.5.5% |
| Stage IV | 22 | 17.6% | 83 | 38.7% |
| Unspecified stage | 9 | 7.2% | 3 | 4.2% |
| Tumor size | | | | |
| <2 cm | 2 | 1.6% | 3 | 1.40% |
| 2-5 cm | 19 | 15.2% | 54 | 25.2% |
| >5 cm | 104 | 83.2% | 157 | 73.4% |
| Previous treatment | | | | |
| Prior chemotherapy | 7 | 5.6% | 13 | 6.07% |
| Prior adjuvant therapy | 25 | 20% | 47 | 21.9% |
| Prior surgery | 2 | 1.6% | 19 | 8.8% |
| Disease status | | | | |
| Locally advanced | 66 | 52.8% | 113 | 52.8% |
| Metastatic disease | 35 | 28% | 71 | 33.2% |

Efficacy

Figure 9:
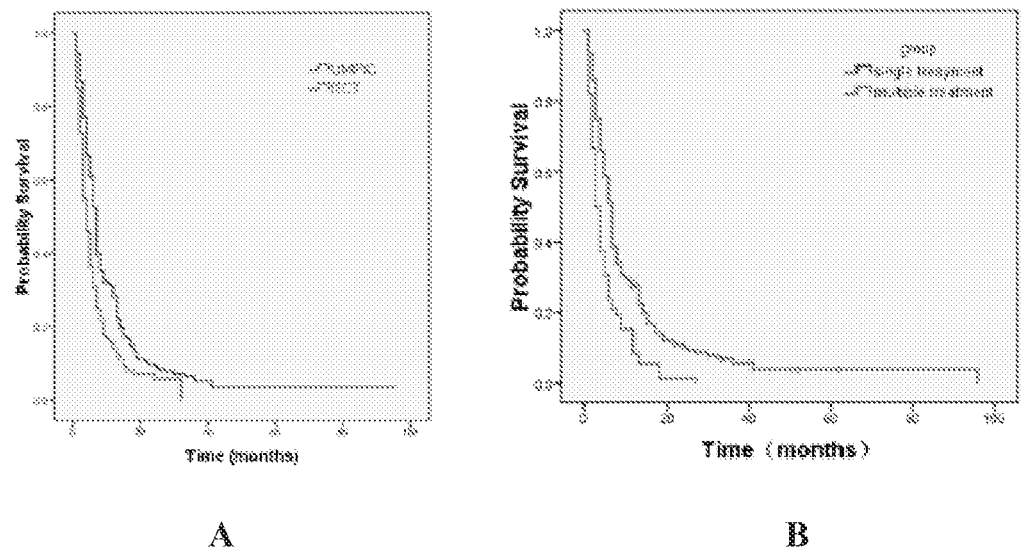
FIG. 9A shows survival probability (Kaplan-Meier). Overall survival (OC) curves in patients treated with tumoricidal chemoimmunotherapy (TCIT) vs. intratumoral chemotherapy (ITCT) groups. p=0.000.
FIG. 9B shows survival probability (Kaplan-Meier). Overall survival (OS) curves in patients with multiple treatments vs. single treatment (P=0.000).

Complete tumor response data was available for analysis in 61 patients who received ITCT and 119 patients who received TCIT. The response rates (CR+PR+SD/TOTAL) were 78.68% and 81.52% in the TCIT and ITCT group respectively, showing no significant difference (Table 15). A few days after therapy, slight size increase of the tumor mass was observed in both groups, which was likely due to inflammatory response induced by coagulations or interactions of malignant cells with the extremely high concentration cytotoxic drug from the local administration (Goldberg et al., *Proc NSTI Nanotech* (2006) 2:1-4; Goldberg et al. *J Pharm Pharmacol* (2002) 54(2):159-180). The median OS (censored observations, surviving patients still in follow-up) was 7.0 months and 4.0 months in TCIT and ITCT groups, respectively [Table 16]. This represents a significant difference between the two groups (P<0.01), with curves (Kaplan-Meier) for both groups depicted in FIG. 9. The 6-month and 1-year survival rates of the TCIT and ITCT groups were 60.8% vs 36.3% and 31.1% vs 15.0% [Table 17]. The survival of the TCIT group was significantly higher than that of the ITCT group.

TABLE 15

Therapeutic response effect of intratumoral chemotherapy (ITCT) and tumoricidal chemotherapy (TCIT)

| Effect | ITCT N | % | TCIT N | % | Total N | % | P |
|---|---|---|---|---|---|---|---|
| CR(n) | 0 | 0 | 0 | 0 | 0 | 0 | 0.650 |
| PR(n) | 5 | 8.19 | 5 | 4.21 | 10 | 5.56 | |
| SD(n) | 43 | 70.49 | 92 | 77.31 | 135 | 75 | |
| PD(n) | 13 | 21.32 | 22 | 18.48 | 35 | 19.44 | |
| Total | 61 | 100.00 | 119 | 100.00 | 180 | 100.00 | |
| CR + PR (%) | | 8.19 | | 4.21 | | 5.56 | |
| CR + PR + SD (%) | | 76.86 | | 81.52 | | 80.56 | |

TABLE 16

Survival time of patients receiving TCIT and ITCT

| GROUP | N | mean survival/ month | median survival/ month | P |
|---|---|---|---|---|
| TCIT | 214 | 12.17 | 7.00 | 0.0015 |
| ITCT | 125 | 6.17 | 4.00 | |
| TOTAL | 339 | 10.76 | 6.00 | |

TABLE 17

Comparison of patient survival time between TCIT and ITCT

| GROUP | N | 6-month survival rate/% (%) | $\chi^2$ | P | 1-year survival rate/% (%) | $\chi^2$ | P |
|---|---|---|---|---|---|---|---|
| TCIT | 214 | 60.8 | 6.5840 | 0.000 | 31.1 | 6.89 | 0.002 |
| ITCT | 125 | 36.3 | | | 15.0 | | |
| TOTAL | 339 | 52.3 | | | 26.07 | | |

Figures 1, 10:
Figures 1, 10:
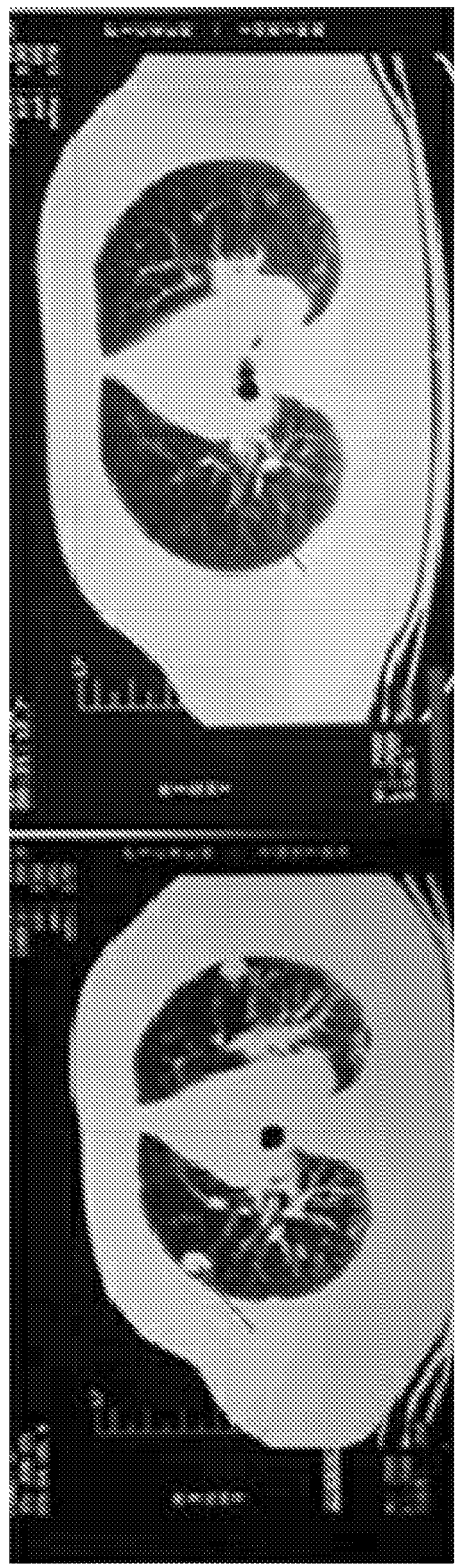
Figures 2, 10:
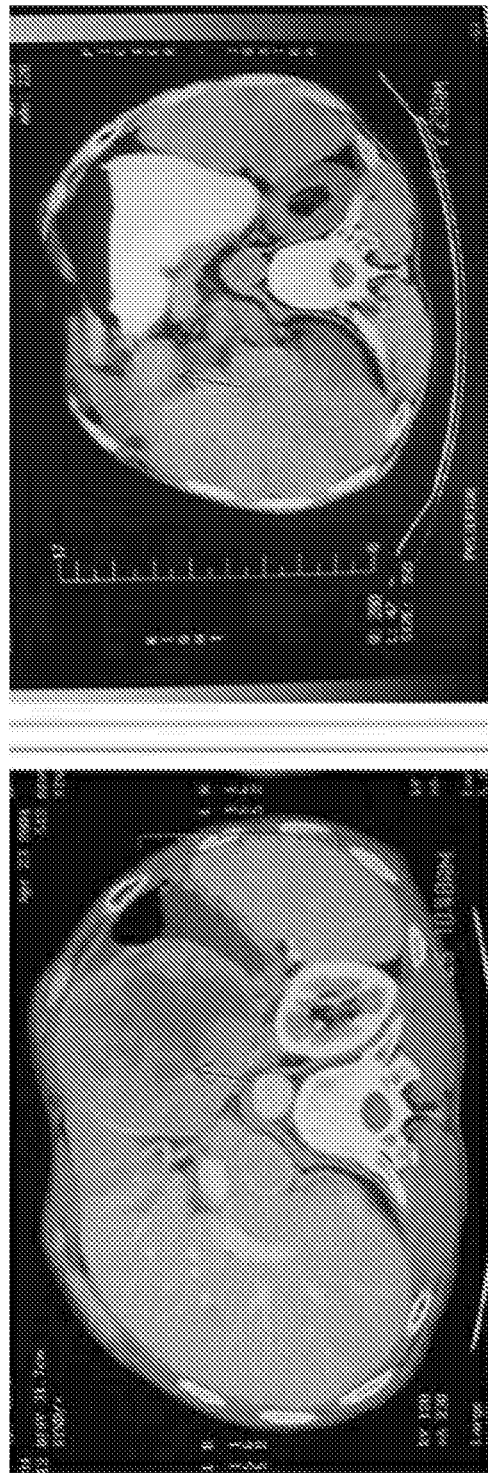

One patients had a systemic response to distant tumor with TCIT in clinical observation. One patient with bilateral pulmonary metastatic lesions received 11 TCIT treatments that targeted the primary tumor; he survived more than five years from the time of diagnosis. The patient had disease regression in primary mass as well as distant sites in the lungs which were not injected [FIG. 10], further supporting the conception of "abscopal effect" caused by hapten-enhanced systemic immune response.

The median survival time of the multiple-therapy group is twice that of the single group (7.0 months vs 3.0 months), showing a significant difference (P<0.01). Also the 6-month and 1-year survival rates of the multiple-therapy group showed a significant improvement over that of the single group (P<0.01) [Tables 16-19] and [FIG. 9].

TABLE 18

Comparison of pateint survival time between single and multiple (≥2) treatments

| Times | N | mean survival/ month | median survival/ month | $\chi^2$ | P |
|---|---|---|---|---|---|
| Single | 72 | 5.26 | 3.00 | 25.108 | <0.0001 |
| Multiple | 267 | 12.18 | 7.00 | | |
| Total | 339 | 10.84 | 6.00 | | |

TABLE 19

Comparison of the efficacy between single and multiple (≥2) treatments

| Times | N | 6-month survival rate/% (%) | $\chi^2$ | P | 1-year survival rate/% (%) | $\chi^2$ | P |
|---|---|---|---|---|---|---|---|
| Single | 72 | 30.8 | 18.2679 | <0.0001 | 15.28 | 7.6871 | 0.0056 |
| Multiple | 267 | 60.3 | | | 32.20 | | |
| Total | 339 | 54.0 | | | 24.07 | | |

Common complications included temporary mild fever (not over 38° C.) for a few hours, minor pain at injection area and minimal hemorrhage around the tumor and needle track after therapy. No other significant systemic or local adverse effects were observed. Common chemotherapy side effects such as myeloid suppression, neutropenia, thrombocytopenia, GI toxicity, and apparent loss of hair and/or appetite were not seen.

HCC is a potentially ideal tumor for targeting by immune-based therapies (Butterfield L H, Gastroenterology 12 (2004) (Suppl 1) 25:232-241), therefore immunotherapy approaches may play a crucial role in its treatment. To date the immunotherapeutic strategies for HCC include the administration of immune stimulator cytokines (Shiratori et al., Ann Intern Med (2003) 138(4):299-306), gene therapy with cytokines and co-stimulatory molecules (Cao et al., Stem Cells (1998) 16(Suppl 1):251-260), immunotherapy with dendritic cells loaded with specific tumor antigen (Melcher et al., Cancer Res (1999) 59:2802-2805), and stimulation with immunogenic vaccines or antibodies (Matar et al., J Biomed Sci (2009) 16:30).

Current mono-immunotherapy (as well as standard chemotherapy) shows limited effectiveness in current late stages of HCC therapy due to tumor loads over the capability for immunotherapy. Effective combinations of immunotherapy and chemotherapy (or chemoimmunotherapy) remain to be explored.

Rescigno, et al. showed that cytotoxic drugs are not always detrimental to immune system; they can actually enhance anti-tumor immune response by increasing tumor antigen presentation and depleting tumorpromoting regulatory T cells, as well as through other mechanisms (Rescigno et al., Biochim Biophys Aca (2007) 1776(1):108-123). Moreover, chemoimmunotherapy has also demonstrated synergistic efficacy in the treatment of HCC (Lau et al., Ann Surg (2001) 233(2):236-241), lymphoma (Bujanda et al., Clin Transl Oncol (2009) 11(9):604-608) and leukemia (Schulz et al., Blood (2002) 100:3115-3120). The TCIT examined in this clinical study is a patented therapeutic method with a regimen for solid tumor indications, utilizing patient-specific autologous tumor-associated antigens in vivo of the patient's body as a self-vaccination for tumor-specific response.

Chemoembolization is an interventional radiology approach for liver cancer (Clark T W I, Semin Intervent Radiol (2006) 23(2): 119-25). If the tumor is too large, however, or doesn't have blood vessels, this therapy is unsuitable. Chemoembolization can block the blood vessels with oil-drug emulsion. The drug would need to leave the oil to enter the tumor to kill the cancer cells. When the oil-drug combination moves to the whole body it produces side effects, so we developed TCIT, needing no catheter or oil-drug emulsion.

First, after TCIT the oxidant can effectively change extracellular matrix (EM) instantly and alter morphological and biochemical components of the tumor cells such as collagen and other high-molecular weight substances via coagulation. This leads to transformation into a soft, semisolid or solid mass, stopping tumor metabolism and causing fibrosis [FIG. 7]. Coagulation also inhibits blood flow and entraps the injected drugs at higher concentrations within the coagulated tumors. This improves drug utilization by extending the duration of the drug as well as systemic drug exposure through sustained drug release, also reducing its toxicity. Meanwhile, the drug Ara-C will continue to kill the tumor cells which are not killed by coagulation. Intratumoral therapy, as an obvious and attractive alternative to systemic treatment, has been approved for clinical use (Klutz et al., *Hum Gene Ther* (2011) 22(11): 1403-1412). Intratumoral delivery of anticancer drugs can significantly increase the local accumulation of drug (up to 10-100 times more than systemic administration) (Goldberg et al., *J Pharm Pharmacol* (2002) 54(2):159-180). The sustained-release phenomenon was observed in our clinical treatment. We separately injected intratumoral Ara-c combined with an oxidant and the Ara-c alone in two tumor masses in the same liver of an HCC patient, and found the drug retention at 82% vs 16% at 12 hours in each tumor, and 60%0 vs 0% within the tumor at 24 hours in each tumor after injection, respectively [FIG. 8]. Therefore, it is particularly important to note that the advantage of this approach, including highly sustained and homogeneous drug diffusion, can be obtained.

It is believed that the procedures of coagulation and drugs sustained in tumors play a powerful role in chemically debulking tumor main mass (FIG. 10) and provide an opportunity for the patient's own immunotherapy to take place against microtumors (no more than 108 tumor cells) in which immunotherapy could make a difference.

Secondly, as has been reported, there is "abscopal effect;" the regression of distant tumor after localized treatment (Demaria et al., *Int J Radiat Oncol Biol Phys* (2004) 58:862-870). In this clinical study, hapten can induce an immunological (correlates abscopal-like) antitumor response, which was documented in an HCC patient with bilateral pulmonary metastases. It means TCIT-induced immunological response can be effective against micro tumors at a differently challenged site even the imaging-invisible or unapproachable tumors. Charles Ludgate (Ludgate, C M, *Clin Cancer Res* (2012) 18:4522-4525) noted that pathogen-associated molecular patterns (PAMPs) and damage-associated molecular patterns (DAMPs) may have the desired abscopal effect on metastatic tumor sites by evoking an acute anticancer immune response using an "endogenous" vaccine approach. A similar result was mentioned in the clinical reports (Postow et al., *N Engl J Med* (2012) 366:925-931; Abei et al., *Radiation Oncology* (2013) 8:239).

Our results showed that TCIT improved survival. The 6-month and 1-year survival rates of TCIT and ITCT groups were 60.8% vs 36.3% and 31.1% vs 15.0% (P<0.01) (see Table 16). Our earlier animal studies showed that there is a significant boost to systemic immunity after TCIT, especially for the number of CD4$^+$ T cells. In the case with abscopal effect, we treated only the primary tumor in liver resulting in the disappearance of two lung metastatic lesions. The synergistic strategy may mainly work with hapten as the immune adjuvant to integrate local chemotherapeutic agents by activating systemic anti-tumor immunity.

When multiple autologous tumor-associated antigens were released from the apoptotic or necrotic tumor cells caused by coagulation and the cytotoxic drug, theoretically they can trigger an immune response as a self-vaccination. Studies have reported, however, that cell death can be a priming event for T cell response and induce potent immunity (Nowak et al., *Adv Drug Deliv Rev* (2006) 58(8):975-990; Lake et al, *Nat Rev Cancer* (2005) 5(5):397-405). In the presence of an immunological modulator (i.e., small-molecule hapten inlaying the denatured tumor), the lysed tumor cells in the resulting depot were modified with hapten and generated stronger tumor-associated antigens referred to as an autologous tumor vaccine (making the tumor itself more immunogenic). Accordingly, the systemic immunity against patient-specific tumor associated antigens was boosted by significantly increasing active antigen-producing cells (APCs) (including dendritic cells (DCs) and macrophage), which is recognized by T cells and NK cells. This fights active (or pathogenic) tumor cells in and around the primary tumor, as active tumor cells are not yet killed by initial coagulation.

Figure 11B:
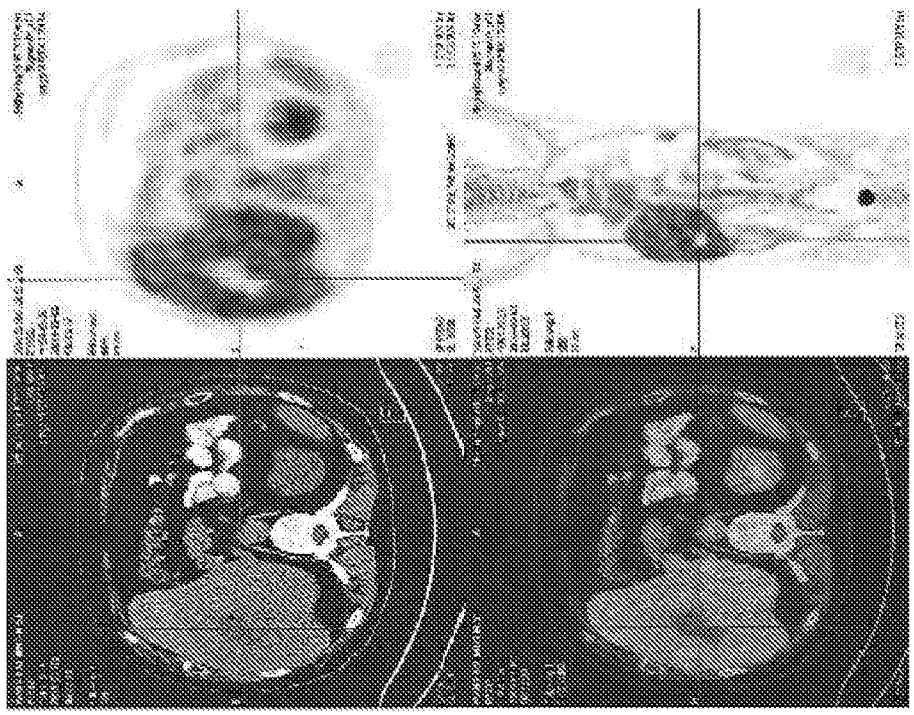
FIG. 11A and FIG. 11B show comparison Pet/Ct before therapy and after therapy. After three TCIT patient's PET/CT showed that hepatocellular carcinoma had necrosis with F18 more activity cycle the necrosis comparison with PEC/CT before TCIT, it means that tumor dying and inflammation induced by TCIT.
Figure 11A:
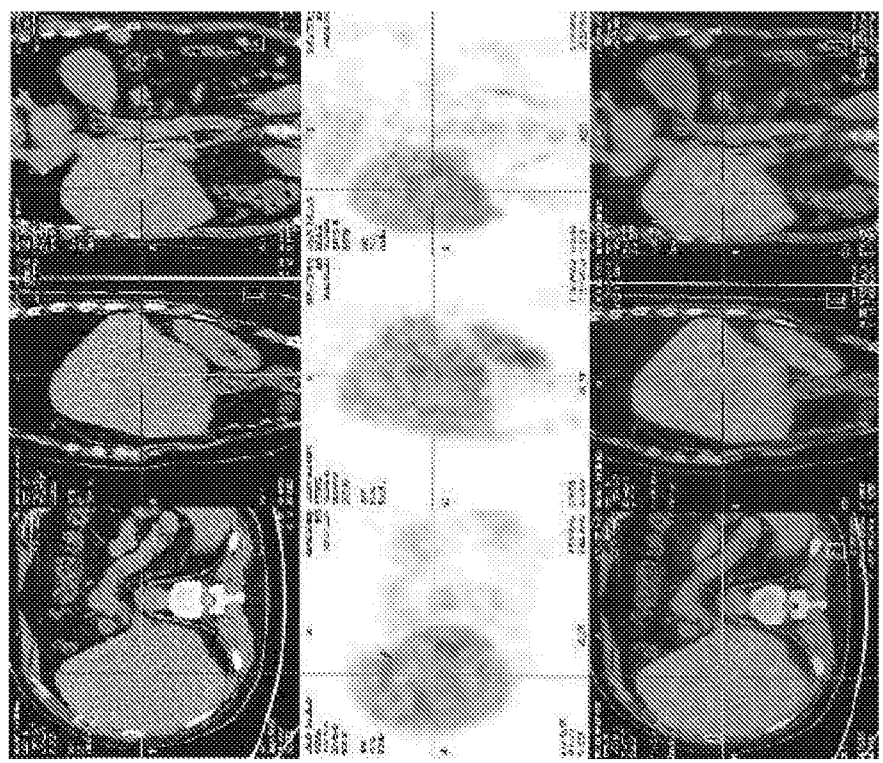

Inflammatory response may involve anti-tumor immunity. Coagulation mass for inflammatory tissue with cytokine and chemokine release are attracting dendritic and other antigen-presenting cells to meet the antigens released from the dead tumor to drain lymph nodes, driving an adaptive acute immunity to further eradicate cancer cells at distant sites. This clinical study showed that TCIT could induce more inflammatory response in local tumors, resulting in no significant therapeutic effect of TCIT and ITCT groups. It did show significantly increased survival time for the TCIT group. We believe that TCIT-induced inflammatory response with hapten may play an important role in the tumor's autologous vaccine-like function, but this immunological power may be weak to reach significant clinical benefit. So TCIT therapy may need multiple treatments (or immunological cell or core blood cell therapy) as an adjuvant after TCIT treatments do the debulking of main tumor loads (FIG. 11).

In our trial, multiple treatments have demonstrated clinical efficacy and safety with compelling clinical evidence [Tables 17 & 18]. This may attribute to long-term immunological memory induced by constitutively released antigens leading to a more effective anti-tumor response. Furthermore, as the marker of the activated T cells, elevation of the co-stimulator may associate with clinical benefits and overall survival (Carthon et al., *Clin Cancer Res* (2010) 16:2861-2871).

Compared with traditional chemotherapy, the side effects of TCIT include minimal fever, local pain and accidental metastasis in the needle track. The clinical outcome is an improved quality of life. It is better to withdraw the needle while keeping the syringe filled with compound solution, in an effort to prevent backflow of metastatic cells. In addition, the shortest distance and an ideal angle are vital to puncture into the tumor. This is a prerequisite to avoid complications. The latent metastatic cells along the needle track are killed by compounded solution along the needle track. We did not find any case with local metastasis in our study after taking this step. In an earlier study we found one case of metastasis under the skin after withdrawing the needle without contained compound solution. This is supported by other studies such as "clinical experience with finest needle aspiration biopsy with little evidence of complications attributable to needle track metastasis" (Goldberg et al., *J Pharm Pharmacol* (2002) 54(2):159-180).

In conclusion, TCIT provides combined hapten-heightened chemoimmunotherapy with a safe, efficacious therapy, especially for patients with advanced stages. It creates a way to decrease the cardinal mass and boost the patient's own immunological power to fight against micro cancers in a specific and innovative manner.

Example 4

Chemical Surgery by Sequential Treatment with Multiple Haptens

Cancer patients with solid tumor are treated with multiple sessions of chemical surgery at bi-weekly intervals. For each treatment session, the patent is treated with an oxidant and a different hapten. This treatment regimen reduces the development of drug resistance and improves the responsiveness in the cancer patients.

Materials and Methods

Patient Selection and Data Collection

Patients are informed of the study procedure details and agreed to participate by signing informed consent. Confirmed by imaging and pathologic examination, patients with the solid tumor are retrospectively analyzed. A control group is set up which receives the same hapten for each treatment session. All patients are approved by the hospital ethics committee. Data are collected from case report forms (CRFs) completed by hospital physicians. Collected data include clinical characteristics, follow-up time and response data. For each patient the first follow-up visit is scheduled two weeks after treatment completion and then on one-month intervals. Median follow-up time is 6 months. The records are updated during each follow-up visit.

Chemical Surgery Preparation

The combined drugs are freshly prepared before each injection with a clinically approved regimen of an oxidant and a hapten for intratumoral delivery. Hydrogen peroxide is used as the redox agent. For the first treatment, DNP is used as the hapten. For the second treatment, Benzylpenicillin is used as the hapten. For the third treatment, Procainamide Hydrochloride is used as the hapten. For the fourth treatment, Hydralazine Hydrochloride is used as the hapten. The drugs are injected into the tumor with a spinal needle linked to a dilator as a high pressure syringe (BD Inc., Calif.).

Treatment Delivery

All patients have either a pretreatment ultrasound or CT scan of the liver as a baseline. Routine examination of cardiopulmonary function is also done before the treatment. The laboratory blood tests include hepatitis B and C virus antigen/antibodies, serum alpha-fetoprotein (AFP), serum albumin (Alb), serum total bilirubin (Tbil), and alanine aminotransferase (ALT). Bucinnazine hydrochloride (100 mg) and hemocoagulase atrox for injection (1 KU) are injected intramuscularly. The patients are kept in supine or lateral decubitus positions to accurately locate the injection sites. After routine skin preparation, draping and local anesthesia with 2% lidocaine, under ultrasound or CT guidance, the spinal needle is introduced into the tumor in a certain angle. When the needle reaches the necessary depth of tumor, the drugs are delivered through the dilator to the needle at the level of atmospheric pressure to facilitate diffusion of the drug within the tumor. Having injected with the combined solution of twice the tumor diameter (ml), the physicians observes the intratumoral drug diffusion and related complications such as intratumoral hemorrhage and bleeding around the pin track. The whole procedure takes about 30-45 minutes. Patients are closely watched for two hours post-injection for any side effects and are further monitored for 5-7 days to decide whether more injections are needed. Injection session is repeated at two-week intervals for up to a total of four sessions. The patients are re-examined by CT or ultrasound 4-6 weeks after the last treatment.

Assessment

The response to treatment is evaluated by solid tumor effect evaluation criterion of EROTC (European Organization for Research and Treatment of Cancer) and RECIST (Response Evaluation Criteria in Solid Tumors) made by NCI (National Cancer Institute) (US and Canada) in October 1999 (Duffaud et al., *Bull Cancer* (2000) 87(12):881-886).

Statistical Analysis

Statistical analysis is performed. The primary objective is to evaluate the overall survival (OS), which is defined as the duration from the first hospitalization date to the death date and estimated according to the Kaplan-Meier analysis. Secondary end point time is response rate at 4-6 weeks, defined as the proportion of patients with a complete response (CR), partial response (PR), or stable disease (SD) according to RECIST (version 1.0). Response rates and survival rate are analyzed and statistical differences between groups are based on the Chi-square test. The statistical analysis is conducted with SPSS 17.0 statistical software (SPSS Inc., Chicago, Ill., USA); P value of <0.05 is considered to indicate statistical significance.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

All publications, including patent documents and scientific articles, referred to in this application and the bibliography and attachments are incorporated by reference for the referenced materials and in their entireties for all purposes to the same extent as if each individual publication were individually incorporated by reference.

Citation of the above publications or documents is not intended as an admission that any of the foregoing is pertinent prior art, nor does it constitute any admission as to the contents or date of these publications or documents.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

Terms and phrases used in this document, and embodiments thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless apparent from the context or expressly stated otherwise. Similarly, a group of items linked with the conjunction "or" should not be read as requiring mutual exclusivity among that group, but rather should also be read as "and/or" unless it is apparent from the context or expressly stated otherwise. Furthermore, although items, elements or components of the invention may be described or claimed in the singular, the plural is contemplated to be within the scope thereof unless limitation to the singular is explicitly stated. For example, "at least one" may refer to a single or plural and is not limited to either. The presence of broadening words and phrases such as "one or more," "at least," "but not limited to", or other like phrases in some instances shall not be read to mean that the narrower case is intended or required in instances where such broadening phrases may be absent.

What is claimed is:

1. A method for treating neoplasm in a mammal, comprising multiple treatments, wherein each treatment comprises intratumorally administering to the neoplasm an effective amount of a pharmaceutical composition comprising:
   a redox agent;
   a hapten; and
   at least two chemotherapeutic agents,
   wherein a different hapten is used in each treatment, and wherein a first treatment uses 2,4-dinitrophenol (DNP) as a first hapten, a second treatment uses Benzylpenicillin as a second hapten, a third treatment uses Procainamide Hydrochloride as a third hapten, and a fourth treatment uses Hydralazine Hydrochloride as a fourth hapten.

2. The method of claim 1, wherein the haptens of the multiple treatments are selected from the group consisting of 2,4-dinitrophenol (DNP), Benzylpenicillin, Procainamide Hydrochloride, Hydralazine Hydrochloride, Quinidine, Levamisole Hydrochloride, Inosine Pranobex, Aluminium Hydroxide, trinitrophenol (TNP), N-iodoacetyl-N'-(5-sulfonic 1-naphtyl)ethylene diamine (AED), and dinitrofluorobenzene (DNFB).

3. The method of claim 1, wherein the redox agent is selected from the group consisting of hydrogen peroxide ($H_2O_2$), stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS), carbamide peroxide.

4. The method of claim 1, wherein the at least two chemotherapeutic agents are selected from the group consisting of Mechlorethamine, Cyclophosphamide, Melphalan (L-sarcolysin), Chlorambucil, Hexamethylmelanine, Thiotepa, Busulfan, Carmustine (BCNU), Lomustine (CCNU), Semustine (methyl-CCNU), Streptozocin (streptozotocin), Dacarbazine (DTIC; dimethyltriazenoi-midazole-carboxamide), Methotrexate (amethopterin), Fluorouacil (5-fluorouracil; 5-FU), Floxuridine (fluorode-oxyuridine; FUdR), Cytarabine (cytosine arabinoside, or Ara-C), Mercaptopurine (6-mercaptopurine; 6-MP), Thioguanine (6-thioguanine; TG), Pentostatin (2'-deoxycoformycin), Vinblastine (VLB), Vincristine, Etoposide, Dactinomycin, Daunombicin, Daunomycin, Doxorubicin, Bleomycin, Plicamycin (mithramycin), Mitomycin (mitomycin C), L-Asparaginase, Interferon-alfa, Cisplatin (cis-DDP), Carboplatin, Mitoxantrone, Hydroxyurea, Procarbazine, Mitotane (o,p'-DDD), Prednisone, Hydroxyprogesterone caproate, Medroxyprogesterone acetate, Megestrol acetate, Diethylstilbestrol, Ethinyl estradiol, Tamoxifen, Testosterone propionate, Fluoxymesterone, Flutamide, and Leuprolide.

5. The method of claim 1, wherein the multiple treatments are conducted at weekly intervals.

6. The method of claim 1, wherein at least 2 treatments are conducted.

7. The method of claim 1, wherein the survival rate of the patients with multiple treatments is improved in comparison to the survival rate of the patients with single treatment.

8. The method of claim 1, wherein the mean survival of the patients with multiple treatments is improved in comparison to the mean survival of the patients with single treatment.

9. The method of claim 1, comprising forced distribution of the pharmaceutical composition in the neoplasm.

10. The method of claim 9, wherein the pharmaceutical composition is administered to the neoplasm using a high pressure syringe that is powered at about 4 AMP to about 6 AMP.

11. The method of claim 1, wherein the pharmaceutical composition is distributed throughout the matrix of the whole tumor.

12. The method of claim 1, wherein the neoplasm to be treated is selected from the group consisting of adrenal gland, anus, bile ducts, bladder, bone, breast, buccal, cervix, colon, ear, endometrium, esophagus, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, stomach, testes, thyroid, tonsil, urethra, uterus, vagina, and vulva.

13. The method of claim 1, wherein the neoplasm to be treated is solid tumor larger than $10^8$ cells.

14. The method of claim 1, wherein the neoplasm is induced into necrosis or is induced into fibrosis.

15. The method of claim 1, further comprising administering an immune response potentiator to the neoplasm, and wherein the immune response potentiator is selected from the group consisting of Bacille Calmette-Guerin (BCG); *Corynebacterium Parvum; Brucella abortus* extract; glucan; levamisole; tilorone; an enzyme selected from the group consisting of *Vibrio cholera* neuramidase (VCN), Papain, β-Gal and ConA; a non-virulent Newcastle virus; and a polysaccharide selected from the group consisting of sizofuran (SPG), schizophyllan, mannan, lentinan, Su-polysaccharide (Su-Ps) and mannozym.

16. The method of claim 1, whereby an immune response is generated against the neoplasm and the immune response comprises is a humoral or cellular immune response.

17. The method of claim 1, wherein the at least two chemotherapeutic agents are Cytarabine (cytosine arabinoside, or Ara-C) and Daunomycin.

\* \* \* \* \*